United States Patent
Chou et al.

(10) Patent No.: US 10,201,311 B2
(45) Date of Patent: Feb. 12, 2019

(54) EXPANDABLE CATHETER ASSEMBLY WITH FLEXIBLE PRINTED CIRCUIT BOARD (PCB) ELECTRICAL PATHWAYS

(71) Applicant: Acutus Medical, Inc., San Diego, CA (US)

(72) Inventors: Derrick Ren-Yu Chou, San Diego, CA (US); Timothy J. Corvi, Carlsbad, CA (US); Marcus Frederick Julian, Vista, CA (US); Darryl Alan Knight, San Diego, CA (US); Ricardo David Roman, Chula Vista, CA (US); J. Christopher Flaherty, Auburndale, FL (US)

(73) Assignee: ACUTUS MEDICAL, INC., Carlsbad, CA (US)

( * ) Notice: Subject to any disclaimer, the term of this patent is extended or adjusted under 35 U.S.C. 154(b) by 556 days.

(21) Appl. No.: 14/762,944

(22) PCT Filed: Feb. 7, 2014

(86) PCT No.: PCT/US2014/015261
§ 371 (c)(1),
(2) Date: Jul. 23, 2015

(87) PCT Pub. No.: WO2014/124231
PCT Pub. Date: Aug. 14, 2014

(65) Prior Publication Data
US 2015/0366508 A1 Dec. 24, 2015

Related U.S. Application Data

(60) Provisional application No. 61/762,363, filed on Feb. 8, 2013.

(51) Int. Cl.
*A61B 8/12* (2006.01)
*A61B 5/00* (2006.01)
(Continued)

(52) U.S. Cl.
CPC .......... *A61B 5/6858* (2013.01); *A61B 5/0422* (2013.01); *A61B 5/6859* (2013.01);
(Continued)

(58) Field of Classification Search
CPC ... A61B 5/6858; A61B 5/0422; A61B 5/6853; A61B 5/6859; A61B 18/1492;
(Continued)

(56) References Cited

U.S. PATENT DOCUMENTS 5,041,973 A     8/1991  Lebron et al.
5,156,151 A  *  10/1992 Imran .................. A61N 1/056
                                                    600/375
(Continued)

FOREIGN PATENT DOCUMENTS

CA          2829626       9/2012
CN        201223445       4/2009
(Continued)

OTHER PUBLICATIONS

Japanese Office Action dated Jun. 27, 2017 issued in corresponding Japanese Application No. 2015-530101, with English language translation.
(Continued)

*Primary Examiner* — Lee S Cohen
*Assistant Examiner* — Erin M Cardinal
(74) *Attorney, Agent, or Firm* — Onello & Mello, LLP

(57) ABSTRACT

Provided is a flex-PCB catheter device that is configured to be inserted into a body lumen. The flex-PCB catheter comprises an elongate shaft, an expandable assembly, a flexible printed circuit board (flex-PCB) substrate, a plurality of electronic components and a plurality of communication paths. The elongate shaft comprises a proximal end and a distal end. The expandable assembly is configured to transition from a radially compact state to a radially
(Continued)

expanded state. The plurality of electronic elements are coupled to the flex-PCB substrate and are configured to receive and/or transmit an electric signal. The plurality of communication paths are positioned on and/or within the flex-PCB substrate. The communication paths selectively couple the plurality of electronic elements to a plurality of electrical contacts configured to electrically connect to an electronic module configured to process the electrical signal. The flex-PCB substrate can have multiple layers, including one or more metallic layers. Acoustic matching elements and conductive traces can be includes in the flex-PCB substrate.

30 Claims, 15 Drawing Sheets

(51) Int. Cl.
    *A61N 1/05*     (2006.01)
    *A61B 18/14*     (2006.01)
    *A61B 5/042*     (2006.01)
    *A61B 8/00*     (2006.01)
    *A61B 18/12*     (2006.01)
    *A61N 7/02*     (2006.01)
    *A61B 18/00*     (2006.01)
    *A61N 7/00*     (2006.01)

(52) U.S. Cl.
    CPC ............... *A61B 8/12* (2013.01); *A61B 8/445* (2013.01); *A61B 8/4477* (2013.01); *A61B 8/4494* (2013.01); *A61B 18/1492* (2013.01); *A61N 1/056* (2013.01); *A61B 8/4272* (2013.01); *A61B 18/12* (2013.01); *A61B 2018/00267* (2013.01); *A61B 2018/00351* (2013.01); *A61B 2018/00404* (2013.01); *A61B 2018/00577* (2013.01); *A61B 2562/0209* (2013.01); *A61B 2562/222* (2013.01); *A61B 2562/227* (2013.01); *A61N 7/022* (2013.01); *A61N 2007/0078* (2013.01)

(58) Field of Classification Search
    CPC .............. A61B 8/445; A61B 8/4477; A61B 2018/00214–2018/00267; A61B 2018/00351; A61B 8/4494; A61B 2018/1467; A61B 2018/0016; A61B 2018/00178; A61N 1/056
    See application file for complete search history.

(56) References Cited

U.S. PATENT DOCUMENTS

| | | | |
|---|---|---|---|
| 5,482,472 A | 1/1996 | Garoni et al. | |
| 5,499,981 A * | 3/1996 | Kordis | A61B 5/0422 606/41 |
| 5,555,883 A | 9/1996 | Avitall | |
| 5,595,183 A | 1/1997 | Swanson et al. | |
| 5,601,084 A | 2/1997 | Sheehan et al. | |
| 5,647,367 A | 7/1997 | Lum et al. | |
| 5,662,108 A | 9/1997 | Budd et al. | |
| 5,722,402 A | 3/1998 | Swanson et al. | |
| 5,722,416 A | 3/1998 | Swanson et al. | |
| 5,740,808 A | 4/1998 | Panescu et al. | |
| 5,749,833 A | 5/1998 | Hakki et al. | |
| 5,759,158 A | 6/1998 | Swanson | |
| 5,795,298 A | 8/1998 | Vesely et al. | |
| 5,795,299 A | 8/1998 | Eaton et al. | |
| 5,820,568 A | 10/1998 | Willis | |
| 5,876,336 A | 3/1999 | Swanson et al. | |
| 5,928,228 A | 7/1999 | Kordis et al. | |
| 5,968,040 A | 10/1999 | Swanson et al. | |
| 6,014,590 A | 1/2000 | Whayne et al. | |
| 6,024,703 A | 2/2000 | Zanelli et al. | |
| 6,066,096 A | 5/2000 | Smith et al. | |
| 6,086,532 A | 7/2000 | Panescu et al. | |
| 6,107,699 A | 8/2000 | Swanson | |
| 6,187,032 B1 | 2/2001 | Ohyu et al. | |
| 6,188,928 B1 | 2/2001 | Noren et al. | |
| 6,216,027 B1 * | 4/2001 | Willis | A61B 5/0422 600/424 |
| 6,216,043 B1 | 4/2001 | Swanson et al. | |
| 6,240,307 B1 | 5/2001 | Beatty et al. | |
| 6,301,496 B1 | 10/2001 | Reisfeld | |
| 6,400,981 B1 | 6/2002 | Govari | |
| 6,490,474 B1 | 12/2002 | Willis et al. | |
| 6,514,249 B1 | 2/2003 | Maguire et al. | |
| 6,640,119 B1 | 10/2003 | Budd et al. | |
| 6,716,166 B2 | 4/2004 | Govari | |
| 6,728,562 B1 | 4/2004 | Budd et al. | |
| 6,772,004 B2 | 8/2004 | Rudy | |
| 6,773,402 B2 | 8/2004 | Govari et al. | |
| 6,824,515 B2 | 11/2004 | Suorsa et al. | |
| 6,826,420 B1 | 11/2004 | Beatty et al. | |
| 6,826,421 B1 | 11/2004 | Beatty et al. | |
| 6,839,588 B1 | 1/2005 | Rudy | |
| 6,895,267 B2 | 5/2005 | Panescu et al. | |
| 6,939,309 B1 | 9/2005 | Beatty et al. | |
| 6,950,689 B1 | 9/2005 | Willis et al. | |
| 6,970,733 B2 | 11/2005 | Willis et al. | |
| 6,978,168 B2 | 12/2005 | Beatty et al. | |
| 6,990,370 B1 | 1/2006 | Beatty et al. | |
| 7,187,964 B2 | 3/2007 | Khoury | |
| 7,285,119 B2 | 10/2007 | Stewart et al. | |
| 7,289,843 B2 | 10/2007 | Beatty et al. | |
| 7,291,146 B2 | 11/2007 | Steinke et al. | |
| 7,505,810 B2 | 3/2009 | Harlev et al. | |
| 7,841,986 B2 | 11/2010 | He et al. | |
| 7,918,793 B2 | 4/2011 | Altmann et al. | |
| 7,953,475 B2 | 5/2011 | Harlev et al. | |
| 8,103,327 B2 | 1/2012 | Harlev et al. | |
| 8,147,486 B2 | 4/2012 | Honour et al. | |
| 8,150,499 B2 | 4/2012 | Gelbart et al. | |
| 8,175,680 B2 | 5/2012 | Panescu | |
| 8,208,998 B2 | 6/2012 | Beatty et al. | |
| 8,360,786 B2 | 1/2013 | Duryea | |
| 8,364,234 B2 | 1/2013 | Kordis et al. | |
| 8,412,307 B2 | 4/2013 | Willis et al. | |
| 8,417,313 B2 | 4/2013 | Scharf et al. | |
| 8,447,377 B2 | 5/2013 | Harlev et al. | |
| 8,454,596 B2 | 6/2013 | Ma et al. | |
| 8,465,433 B2 | 6/2013 | Zwirn | |
| 8,512,255 B2 | 8/2013 | Scharf et al. | |
| 8,700,119 B2 | 4/2014 | Scharf et al. | |
| 8,755,861 B2 | 6/2014 | Harlev et al. | |
| 8,825,130 B2 | 9/2014 | Just et al. | |
| 8,825,134 B2 | 9/2014 | Danehorn | |
| 8,918,158 B2 | 12/2014 | Scharf et al. | |
| 8,934,988 B2 | 1/2015 | Persson et al. | |
| 8,948,837 B2 | 2/2015 | Harlev et al. | |
| 8,979,839 B2 | 3/2015 | De La Rama et al. | |
| 8,989,842 B2 | 3/2015 | Li et al. | |
| 9,011,423 B2 | 4/2015 | Brewster et al. | |
| 9,037,259 B2 | 5/2015 | Mathur | |
| 9,044,245 B2 | 6/2015 | Condie et al. | |
| 9,167,982 B2 | 10/2015 | Scharf et al. | |
| 9,186,081 B2 | 11/2015 | Afonso et al. | |
| 9,186,212 B2 | 11/2015 | Nabutovsky et al. | |
| 9,192,318 B2 | 11/2015 | Scharf et al. | |
| 9,241,687 B2 | 1/2016 | McGee | |
| 9,351,789 B2 | 5/2016 | Novichenok et al. | |
| D758,596 S | 6/2016 | Perryman et al. | |
| 9,474,486 B2 | 10/2016 | Eliason et al. | |
| 9,480,525 B2 | 11/2016 | Lopes et al. | |
| 9,486,355 B2 | 11/2016 | Gustus et al. | |
| 9,492,227 B2 | 11/2016 | Lopes et al. | |
| 9,492,228 B2 | 11/2016 | Lopes et al. | |
| 9,504,395 B2 | 11/2016 | Scharf et al. | |
| 9,526,573 B2 | 12/2016 | Lopes et al. | |
| 9,579,149 B2 | 2/2017 | Kelly et al. | |
| D782,686 S | 3/2017 | Werneth et al. | |

(56) References Cited

U.S. PATENT DOCUMENTS

| | | |
|---|---|---|
| 9,585,588 B2 | 3/2017 | Marecki et al. |
| 9,610,024 B2 | 4/2017 | Scharf et al. |
| 9,675,401 B2 | 6/2017 | Lopes et al. |
| 9,713,730 B2 | 7/2017 | Mathur et al. |
| 9,717,555 B2 | 8/2017 | Chan et al. |
| 9,717,559 B2 | 8/2017 | Ditter et al. |
| 9,757,044 B2 | 9/2017 | Scharf et al. |
| 9,913,589 B2 | 3/2018 | Scharf et al. |
| 9,968,268 B2 | 5/2018 | Scharf et al. |
| 10,004,459 B2 | 6/2018 | Werneth et al. |
| 2001/0007070 A1 | 7/2001 | Stewart et al. |
| 2002/0128565 A1 | 9/2002 | Rudy |
| 2002/0165441 A1 | 11/2002 | Coleman et al. |
| 2003/0036696 A1 | 2/2003 | Willis et al. |
| 2003/0065271 A1 | 4/2003 | Khoury |
| 2003/0078494 A1 | 4/2003 | Panescu et al. |
| 2003/0153907 A1 | 8/2003 | Suorsa et al. |
| 2003/0158477 A1 | 8/2003 | Panescu |
| 2003/0231789 A1 | 12/2003 | Willis et al. |
| 2003/0236466 A1 | 12/2003 | Tarjan et al. |
| 2004/0039312 A1* | 2/2004 | Hillstead .......... A61N 7/02 601/2 |
| 2004/0254437 A1 | 12/2004 | Hauck et al. |
| 2005/0059880 A1 | 3/2005 | Mathias et al. |
| 2005/0113665 A1 | 5/2005 | Mohr et al. |
| 2005/0148836 A1 | 7/2005 | Kleen et al. |
| 2005/0203375 A1 | 9/2005 | Willis et al. |
| 2006/0058663 A1 | 3/2006 | Willis et al. |
| 2006/0058676 A1* | 3/2006 | Yagi .................. A61B 8/12 600/459 |
| 2006/0058692 A1 | 3/2006 | Beatty et al. |
| 2006/0058693 A1 | 3/2006 | Beatty et al. |
| 2006/0084884 A1 | 4/2006 | Beatty et al. |
| 2006/0084970 A1 | 4/2006 | Beatty et al. |
| 2006/0084971 A1 | 4/2006 | Beatty et al. |
| 2006/0084972 A1 | 4/2006 | Beatty et al. |
| 2006/0116576 A1 | 6/2006 | McGee et al. |
| 2007/0060832 A1 | 3/2007 | Levin |
| 2007/0083194 A1 | 4/2007 | Kunis et al. |
| 2007/0106146 A1 | 5/2007 | Altmann et al. |
| 2007/0219551 A1 | 9/2007 | Honour et al. |
| 2007/0232949 A1 | 10/2007 | Saksena |
| 2008/0009758 A1 | 1/2008 | Voth |
| 2008/0287777 A1 | 11/2008 | Li et al. |
| 2009/0024086 A1 | 1/2009 | Zhang et al. |
| 2009/0076483 A1 | 3/2009 | Danehorn |
| 2009/0131930 A1 | 5/2009 | Gelbart et al. |
| 2009/0143651 A1* | 6/2009 | Kallback .......... A61B 5/02007 600/301 |
| 2009/0171274 A1 | 7/2009 | Harlev et al. |
| 2009/0264781 A1 | 10/2009 | Scharf |
| 2010/0076426 A1 | 3/2010 | de la Rama et al. |
| 2010/0094279 A1* | 4/2010 | Kauphusman ....... A61B 5/0422 606/41 |
| 2010/0168578 A1 | 7/2010 | Garson, Jr. et al. |
| 2010/0298690 A1 | 11/2010 | Scharf |
| 2011/0045130 A1 | 2/2011 | Edens et al. |
| 2011/0077526 A1 | 3/2011 | Zwirn |
| 2011/0118726 A1 | 5/2011 | De La Rama et al. |
| 2011/0125172 A1 | 5/2011 | Gelbart et al. |
| 2011/0172658 A1 | 7/2011 | Gelbart et al. |
| 2011/0213231 A1 | 9/2011 | Hall et al. |
| 2011/0270237 A1 | 11/2011 | Werneth et al. |
| 2012/0078077 A1 | 3/2012 | Harlev et al. |
| 2012/0082969 A1 | 4/2012 | Schwartz et al. |
| 2012/0143298 A1 | 6/2012 | Just et al. |
| 2012/0165667 A1 | 6/2012 | Altmann et al. |
| 2012/0172859 A1 | 7/2012 | Condie et al. |
| 2012/0184863 A1 | 7/2012 | Harlev et al. |
| 2012/0271138 A1* | 10/2012 | Kordis .............. A61B 5/0422 600/375 |
| 2012/0271139 A1 | 10/2012 | Kordis et al. |
| 2012/0277574 A1 | 11/2012 | Panescu |
| 2012/0310064 A1 | 12/2012 | McGee |
| 2013/0006238 A1 | 1/2013 | Ditter et al. |
| 2013/0085361 A1* | 4/2013 | Mercanzini ........ A61B 5/04001 600/377 |
| 2013/0096432 A1 | 4/2013 | Hauck |
| 2013/0158537 A1 | 6/2013 | Deladi et al. |
| 2013/0165916 A1 | 6/2013 | Mathur |
| 2013/0172715 A1 | 7/2013 | Just et al. |
| 2013/0178851 A1 | 7/2013 | Lopes et al. |
| 2013/0190587 A1 | 7/2013 | Lopes et al. |
| 2013/0197614 A1 | 8/2013 | Gustus et al. |
| 2013/0225983 A1 | 8/2013 | Willis et al. |
| 2013/0226017 A1 | 8/2013 | Scharf et al. |
| 2013/0245621 A1 | 9/2013 | Persson et al. |
| 2013/0253298 A1 | 9/2013 | Harlev et al. |
| 2013/0267853 A1* | 10/2013 | Dausch ............... B06B 1/0607 600/466 |
| 2013/0274582 A1 | 10/2013 | Afonso et al. |
| 2013/0282084 A1 | 10/2013 | Mathur et al. |
| 2013/0304062 A1 | 11/2013 | Chan et al. |
| 2013/0304065 A1 | 11/2013 | Lopes et al. |
| 2013/0310827 A1 | 11/2013 | Brewster et al. |
| 2013/0330701 A1 | 12/2013 | Rubinstein et al. |
| 2014/0024910 A1 | 1/2014 | Scharf et al. |
| 2014/0121470 A1 | 5/2014 | Scharf et al. |
| 2014/0180150 A1 | 6/2014 | Scharf et al. |
| 2014/0257069 A1 | 9/2014 | Eliason et al. |
| 2014/0275921 A1 | 9/2014 | Harlev et al. |
| 2014/0276733 A1 | 9/2014 | VanScoy et al. |
| 2014/0276746 A1 | 9/2014 | Nabutovsky et al. |
| 2014/0276789 A1* | 9/2014 | Dandler ............. A61B 18/1492 606/41 |
| 2014/0358143 A1 | 12/2014 | Novichenok et al. |
| 2015/0208938 A1 | 7/2015 | Houben et al. |
| 2015/0223757 A1 | 8/2015 | Werneth et al. |
| 2015/0257732 A1* | 9/2015 | Ryan ................. A61B 8/445 600/425 |
| 2015/0257825 A1 | 9/2015 | Kelly et al. |
| 2015/0342491 A1 | 12/2015 | Marecki et al. |
| 2015/0366508 A1 | 12/2015 | Chou et al. |
| 2015/0374252 A1 | 12/2015 | de la Rama et al. |
| 2016/0038051 A1 | 2/2016 | Scharf et al. |
| 2016/0051321 A1 | 2/2016 | Salahieh et al. |
| 2016/0100770 A1 | 4/2016 | Afonso et al. |
| 2016/0128771 A1 | 5/2016 | Ditter et al. |
| 2016/0128772 A1 | 5/2016 | Reinders et al. |
| 2016/0192902 A1 | 7/2016 | Werneth et al. |
| 2017/0035486 A1 | 2/2017 | Lopes et al. |
| 2017/0258347 A1 | 9/2017 | Scharf et al. |
| 2017/0319180 A1* | 11/2017 | Henneken .......... A61B 8/4494 |
| 2018/0055374 A1 | 1/2018 | Scharf et al. |
| 2018/0146948 A1 | 5/2018 | Chou et al. |

FOREIGN PATENT DOCUMENTS

| | | |
|---|---|---|
| CN | 201275144 | 7/2009 |
| EP | 1166714 | 1/2002 |
| EP | 1760661 | 3/2007 |
| EP | 1779787 | 5/2007 |
| EP | 2051625 | 2/2008 |
| EP | 2252203 | 11/2010 |
| EP | 2683293 | 1/2014 |
| JP | 08501477 | 2/1996 |
| JP | 10137207 | 5/1998 |
| JP | 2001070269 | 3/2001 |
| JP | 2002113004 | 4/2002 |
| JP | 2002522106 | 7/2002 |
| JP | 2003511098 | 3/2003 |
| JP | 2004350702 | 12/2004 |
| JP | 2005536313 | 12/2005 |
| JP | 2006-511296 | 4/2006 |
| JP | 2006511296 | 4/2006 |
| JP | 2011504363 | 2/2011 |
| JP | 2011507656 | 3/2011 |
| WO | 94/06349 | 3/1994 |
| WO | 9406349 | 3/1994 |
| WO | 09905971 | 2/1999 |
| WO | 9905971 | 2/1999 |
| WO | 00/07501 | 2/2000 |

(56) References Cited

FOREIGN PATENT DOCUMENTS

| WO | 0007501 | 2/2000 |
|---|---|---|
| WO | 0245608 | 6/2002 |
| WO | 2002045608 | 6/2002 |
| WO | 03026722 | 4/2003 |
| WO | 2004026134 | 4/2004 |
| WO | 2006060613 | 6/2006 |
| WO | 2008014629 | 2/2008 |
| WO | 2009065042 | 5/2009 |
| WO | 2009090547 | 7/2009 |
| WO | 2011136867 | 11/2011 |
| WO | 2012092016 | 7/2012 |
| WO | 2012100184 | 7/2012 |
| WO | 2012100185 | 7/2012 |
| WO | 2012122517 | 9/2012 |
| WO | 2014036439 | 3/2014 |
| WO | 2014124231 | 8/2014 |
| WO | 2014130169 | 8/2014 |
| WO | 2015148470 | 10/2015 |

OTHER PUBLICATIONS

Canadian Office Action dated Nov. 27, 2017 issued in corresponding Canadian Application No. 2829626.
Decision dated Jan. 18, 2018 issued for European Patent Application No. 13176658.6.
Decision dated Jan. 16, 2018 issued for European Patent Application No. 09702094.5.
Office Action dated Jan. 31, 2018 issued for European Patent Application No. 13763151.1.
"Transducer-Electrode Arrangement" Specification, Drawings, Claims and Prosecution History, of U.S. Appl. No. 29/475,273, filed Dec. 2, 2013, by Randell L. Werneth, et al.
Office Action dated Apr. 27, 2016 in corresponding Canadian Application No. 2747859.
European Office Action dated Feb. 29, 2016 issued in corresponding European Application No. 07 785 075.8-1657.
European SR dated Sep. 29, 2014, issued in European Application No. 13176658.6.
Office Action dated Mar. 9, 2016 in corresponding European Patent Application No. 13176658.6.
Examiner's Report dated Dec. 22, 2015 in related Canadian Application No. 2656898.
Extended European Search Report dated Jul. 8, 2016 in related European Application No. 14748567.6.
Office Action dated Mar. 9, 2016 in corresponding European Patent Application No. 09702094.5.
Van Oosterom A: "Solidifying the solid angle." 2002 Journal of Electrocardiology 2002 vol. 35 Suppl pp. 181-192 ISSN: 0022-0736.
William G. Stevenson et al: "Recording Techniques for Clinical Electrophysiology" Journal of Cardiovascular Electrophysiology. vol. 16 No. 91, Sep. 2005, pp. 1017-1022.
Patent Examination Report No. 3 dated Sep. 21, 2016 in related Australian Application No. 2012225250.
Extended European Search Report dated Oct. 18, 2017, issued in European Application No. 15768711.
Office Action dated Oct. 10, 2017, issued in Application No. 2015-557091 with machine translation English to English.
Office Action dated Nov. 7, 2017, issued in European Application No. 15768711.
Japanese Office Action dated Sep. 26, 2017 issued in corresponding Japanese Application No. 2017-155346, with English translation.
European Office Action dated Mar. 21, 2017 issued in corresponding European Application No. 07785075.8.
Jackson, JD, "Surface Distributions of Charges and Dipoles and Discontinuities in the Electric Field and Potential", Classical Electrodynamics, 3rd edition, Dec. 1998, pp. 31-34.
Canadian Office Action dated Apr. 26, 2017 issued in corresponding Canadian Application No. 2932956.
Chinese Office Action dated Apr. 17, 2017 issued in corresponding Chinese Application No. 201480018328.4.
Office Action dated Mar. 30, 2017 in corresponding Canadian Application No. 2747859.
Leif et al., "Geometric modeling based on polygonal meshes", Eurographics 2000 Tutorial, Aug. 21, 2000.
Invitation to Pay Additional Fees dated Jan. 5, 2014 in corresponding International Application No. PCT/US2013/057579.
Office Action dated Oct. 4, 2013 in corresponding Canadian Patent Application No. 2,659,898.
ISWRO dated May 20, 2014 in International application No. PCT/US14/15261.
PCT ISRWO dated Jun. 5, 2014, issued in corresponding PCT Application No. PCT/US2013/057579.
European Office Action dated Apr. 28, 2014, issued in corresponding European Application No. 09 702 094.5-1660.
Gupta et al. "Point of view cardiac mapping: utility or futility? Non-contact endocardial mapping" Indian Pacing and Electrophysiology Journal 2:20-32 (2002).
Extended European Search Report for related Application No. 13176558 dated Sep. 29, 2014.
International Search Report and Written Opinion in related Application. No. PCT/US2012/028593 dated Mar. 5, 2013.
International Search Report in related Application No. PCT/IB2009/000071 dated Oct. 7, 2009.
Della Bella et al. "Non-contact mapping to guide catheter ablation of untolerated ventrical tachycardia" European Heart Journal, May 2002, 23(9)742-752.
Pullan et al. "The inverse problem of electrocardiology" Northeastern University Electrical and Computer Engineering, Feb. 23, 2007.
Christoph Scharft et al. Declaration under 37 C.F.R. 1.132, Nov. 15, 2012.
He et al. "An equivalent body surface charge model representing three-dimensional bioeleotrical activity" IEEE Transactions on Biomedical Engineering, 42.7 (1995) pp. 637-646.
Partial European Search Report dated Apr. 29, 2014 in corresponding European Application No. 13176658.
International Search Report dated Sep. 10, 2014 issued in corresponding International Application No. PCT/US14/54942.
International Search Report dated Mar. 10, 2015 issued in corresponding International Application No. PCT/US14/54942.
International Search Report and Written Opinion dated Jun. 26, 205 issued in International Application No. PCT/US2015/022187.
ISRWO dated Aug. 11, 2016 issued in corresponding International Application No. PCT/US2016/032017.
ISRWO dated Aug. 8, 2016 issued in corresponding European Application No. PCT/US2016/031823.
ISRWO dated Aug. 18, 2016 issued in corresponding International Application No. PCT/US16/32420.
ISRWO dated Dec. 12, 2017 issued in corresponding International Application No. PCT/US2017/056064.
ISRWO dated Sep. 25, 2017, issued in Application No. PCT/US17/30922.
ISRWO dated Aug. 4, 2017, issued in Application No. PCT/US17/30915.
Australian Office Action dated Jul. 6, 2017, issued in Australian Application No. 2014/214756.
Australian Office Action dated Jun. 27, 2017 issued in Australian Application No. 2013308531.
Japanese Notice of Allowance dated Jul. 11, 2017 issued in Japanese Application No. 2013-557926.
Japanese Office Action dated Jan. 31, 2017 issued in corresponding Japanese Application No. 2013-557926.
Office Action dated May 30, 2016 in related Australian Patent Application No. 2012225250.
Japanese Office Action dated Aug. 28, 2018 issued in corresponding Japanese Application No. 2016-542062, with machine translation into English.
Australian Examination Report dated Jun. 28, 2018, issued in corresponding Australian Patent Application No. 2014318872.
Japanese Notice of Allowance dated Feb. 27, 2018 issued in corresponding Japanese Application No. 2015-530101, with English language translation.

(56) References Cited

OTHER PUBLICATIONS

Canadian Office Action dated Jan. 22, 2018 issued in corresponding Canadian Application No. 2932956.
Jackson JD, "Classical Electrodynamics", 3rd edition, Dec. 1998, pp. 31-34.
Australian Office Action dated Feb. 26, 2018 issued in Australian Application No. 2017201560.
European Office Action dated Apr. 23, 2018 issued in corresponding European Application No. 07785075.8.
Office Action dated Mar. 17, 2018 issued in corresponding Australian Application No. 2013308531.
Patent Examination Report No. 2 dated Jun. 14, 2018 in related Australian Application No. 2014214756.
International Search Report dated Apr. 21, 2008 in related International Application No. PCT/CH2007/000380.
Japanese Office Action dated Feb. 16, 2016 issued in corresponding Japanese Application No. 2013-557-926, with English language summary.
Japanese Notice of Allowance Jul. 11, 2017 issued in corresponding Japanese Application No. 2013-557-926, with English language summary.
He et al. "An equivalent body surface charge model representing three-dimensional bioelectrical activity" IEEE Transactions on Biomedical Engineering, 42.7 (Jul. 7, 1995) pp. 637-646.
Wolfgang Nolting: Elektrodynamik—Grundkurs Theoretische Physik 3, Springer Spectrum, Feb. 28, 2016, p. 89-91, XP009188752.
Japanese Notice of Allowance dated Sep. 18, 2018 issued in corresponding Japanese Application No. 2015-557091, with English language translation.
Extended European Search Report dated Oct. 4, 2018 issued in corresponding European Application No. 16793503.0.

* cited by examiner

EXPANDABLE CATHETER ASSEMBLY WITH FLEXIBLE PRINTED CIRCUIT BOARD (PCB) ELECTRICAL PATHWAYS

CROSS-REFERENCE TO RELATED APPLICATIONS

The present application claims priority under 35 USC 119(e) to U.S. Provisional Patent Application Ser. No. 61/762,363, entitled EXPANDABLE CATHETER ASSEMBLY WITH FLEXIBLE PRINTED CIRCUIT BOARD (PCB) ELECTRICAL PATHWAYS, filed Feb. 8, 2013, which is incorporated herein by reference by its entirety.

The present application, while not claiming priority to, may be related to U.S. Patent Application Ser. No. 61/695,535, entitled SYSTEM AND METHOD FOR DIAGNOSING AND TREATING HEART TISSUE, filed Aug. 31, 2012, which is incorporated herein by reference by its entirety.

FIELD OF INTEREST

The invention relates to the field of medical devices used within the body, and more particularly to the field of medical devices comprising expandable assemblies, e.g., such as expandable catheters used in electrophysiology, and methods for using such devices and expandable assemblies.

BACKGROUND

The use of electrodes within a body for measuring certain electrical characteristics of the heart is routinely performed, sometimes referred to as cardiac mapping. And the use of ablation catheters to selectively ablate nerves or tissue, for example, within the body is also routinely performed. Cardiac mapping and ablation are performed separately, using different, specialized devices or systems.

An ablation catheter can be used, for example, in a medical procedure to treat some types of arrhythmias, which are problems with the rate or rhythm of the heartbeat. An ablation catheter is a long, thin, flexible tube that is put into a blood vessel in the arm, groin (upper thigh), or neck of the patient and guided into the heart through the blood vessel. In catheter ablation, radiofrequency (RF) energy is usually used to produce heat that selectively destroys the heart tissue.

For cardiac mapping, as an example, currently electrodes can be localized within the body either by a permanent magnetic field, a magnetic field generated by electromagnets, or an impedance measurement.

The Carto 3 System by Biosense Webster, Inc. is an example of an electromagnetic field measurement system, in accordance with the prior art. Such a system needs specialized electrodes with electromagnetic coils.

The Localisa® Intracardiac Navigation System by Medtronic, Inc. is an example of an impedance measurement system, in accordance with the prior art. (Localisa is registered as a United States trademark by Medtronic Inc.) Such a system can be inaccurate due to tissue anisotropy and respiration.

SUMMARY

According to one aspect, a device that is configured to be inserted into a body lumen comprises an elongate shaft comprising a proximal end and a distal end; an expandable assembly configured to transition from a radially compact state to a radially expanded state; a flexible printed circuit board (flex-PCB) substrate; a plurality of electronic elements coupled to the flex-PCB substrate and configured to at least one of receive or transmit an electrical signal; and a plurality of communication paths positioned at least one of on or within the flex-PCB substrate and selectively coupling the plurality of electronic elements to a plurality of electrical contacts configured to electrically connect to an electronic module configured to process the electrical signal.

The expandable assembly can be further configured for insertion into a heart chamber.

The device can comprise a dipole mapping device.

The device can be insertable in a body lumen selected from a group comprising: a femoral vein; a femoral artery; an intrajugular vein; an intrajugular artery; the Vena Cava; and combinations of these.

The electrical signal can comprise a signal selected from a group comprising: electrical power; an information signal; a sensor signal; a control signal; and combinations of these.

The electronic module is configured to perform a function selected a group comprising: transmitting a power signal; transmitting a drive signal; transmitting an information signal; receiving an information signal; receiving a sensor signal; processing an information signal; analyzing an information signal; and combinations of these.

At least some of the plurality of electronic elements can be fixedly attached to the flex-PCB substrate and/or the expandable assembly.

At least one of the plurality of electronic elements can comprise at least one element selected from a group comprising: an electrode; an ultrasound transducer; an accelerometer; a sensor; a transducer; and combinations of these.

At least one of the plurality of electronic elements can comprise a sensor selected from a group comprising: a temperature sensor; a pressure sensor; a strain gauge; and combinations of these.

At least one of the plurality of electronic elements can comprise a transducer selected from a group comprising: a sound transducer; an ultrasound transducer; an electrode; a heating element; a cooling element; and combinations of these.

The plurality of electronic elements can comprise at least two different types of electronic elements. For example, the at least two types of electronic elements can comprise at least one electrode and at least one ultrasound transducer. The plurality of electronic elements can comprise at least four electrodes and at least four ultrasound transducers. The plurality of electronic elements can comprise at least six electrodes and at least six ultrasound transducers. The plurality of electronic elements can comprise at least eight electrodes and at least eight ultrasound transducers.

At least one of the plurality of electronic elements can comprise at least one electrode. The at least one electrode can comprise an electrode deposited on the flex-PCB substrate. The at least one electrode can comprise an electrode deposited using a deposition process selected from a group comprising: electro-deposition; ion beam deposition; sputtering; and combinations of these. The at least one electrode can comprise a material selected from a group comprising: copper; gold; platinum; iridium; stainless steel; and combinations of these. The at least one electrode can comprise a conductive coating, for example a conductive coating selected from a group comprising: iridium oxide; Platinum Black; PEDOT; carbon nanotubes; and combinations of these.

At least one of the plurality of electronic elements can comprise an ultrasound transducer. The flex-PCB substrate can comprise an electrically conductive pad and the ultrasound transducer can be electrically connected to the electrically conductive pad. The device can further comprise a housing configured to maintain the ultrasound transducer in electrical contact with the conductive pad. The device can further comprise a clip configured to secure the ultrasound transducer to the flex-PCB substrate. The ultrasound transducer can be soldered to the conductive pad.

The plurality of electronic elements can comprise a plurality of ultrasound transducers. The expandable assembly can comprise at least two splines with at least two ultrasound transducers mounted to each spline. The at least two ultrasound transducers mounted to a first spline can be linearly staggered from at least two ultrasound transducers mounted to a second spline, such that a protrusion of an ultrasound transducer on the first spline extends between protrusions of the at least two ultrasound transducers on the second spline.

The plurality of electronic elements can be configured to transmit and/or receive signals from the electronic module via the plurality of communication paths.

The plurality of electronic elements can comprise one or more piezoelectric transducers (PZT). The one or more piezoelectric transducers can comprise a matching layer, an active element on the matching layer, and a backing material on the active element. The matching layer can be a quarter-wave matching layer based on immersion in blood. The matching layer can be part of a metallic layer of the flex-PCB substrate. The plurality of communication paths can comprise conductive traces formed within the flex-PCB substrate. The conductive traces can be formed around pads of the matching layer. The conductive traces can form part of a first metallic layer of the flex-PCB substrate and the matching layer can be a second metallic layer of the flex-PCB substrate.

The expandable assembly can comprise a spline support, and the flex-PCB substrate can be attached to the spline support in one or more locations. For example, the flex-PCB substrate can be attached to the spline support in two or more discrete locations, where at least two of the two or more discrete locations are separated by a region in which the flex-PCB substrate and the spline support are unattached. The device can further comprise an adhesive, at least one crimp, and/or at least one capture element that attaches the flex-PCB substrate to the spline support in the one or more locations.

The flex-PCB substrate can comprise materials selected from a group comprising: polyimide; polyester; nylon; Pebax; liquid crystal polymer; and combinations of these.

The flex-PCB substrate can have a laminate construction, for example a laminate construction comprising multiple layers of conductors.

The flex-PCB substrate can comprise a first layer with a first set of conductors and a second, opposing layer with a second set of conductors. The flex-PCB substrate can further comprise at least one via between the first layer and the second layer.

The plurality of electronic elements can comprise at least one electronic element selected from a group comprising: a multiplexer; a transducer; a sensor; an A/D converter; a D/A converter; an electric to optical signal converter; an optical to electrical signal converter; an analog signal filter; a digital signal filter; an amplification circuit; a pre-amplification circuit; and combinations of these.

The flex-PCB can comprise a distal end where the expandable assembly is positioned; a proximal end comprising the plurality of electrical contacts; and a middle portion therebetween comprising at least portions of the plurality of communication paths, where the middle portion substantially extends into the shaft. The flex-PCB substrate proximal end can be positioned proximal to the shaft proximal end.

The device can further comprise at least one communication conduit, where the at least one communication conduit can comprise a distal end electrically attached to the flex-PCB substrate and an elongate portion that extends through a majority of the length of the shaft. The at least one communication conduit can comprise a conduit selected from a group comprising: a wire; a trace; a coaxial cable; an optical fiber; and combinations of these. The at least one communication conduit can comprise at least one micro coaxial cable.

The flex-PCB can comprise a plurality of splines, and each spline can comprise a connection region comprising a series of electrical connection points, where the connection regions are arranged linearly about a central axis of the expandable assembly, and where at least one of the connection regions are staggered with respect to at least one other connection region.

The device can further comprise a second flex-PCB substrate comprising a second plurality of electronic elements coupled to the second flex-PCB substrate and configured to at least one of receive or transmit an electrical signal and a second plurality of communication paths positioned at least one of on or within the second flex-PCB substrate and selectively coupling the second plurality of electronic elements to the plurality of electrical contacts configured to electrically connect to the electronic module. The expandable assembly can comprise at least a first spline and a second spline, where the first flex-PCB substrate can be attached to the first spline and the second flex-PCB substrate can be attached to the second spline. The first flex-PCB substrate can have a first length and a connection region at a proximal end of the first flex-PCB substrate, and the second flex-PCB substrate can have a second length and a second connection region at a proximal end of the second flex-PCB substrate, and the first and second connection regions can be arranged linearly about a central axis of the expandable assembly, where the second length can be longer than the first length and the first connection region can be positioned at a more proximal location than a location of the second connection region.

The expandable assembly can comprise between two and eight flex-PCB substrates, where each flex-PCB substrate comprises multiple electronic elements from the plurality of electronic elements and multiple communication paths from the plurality of communication paths that couple the multiple electronic elements from each flex-PCB substrate to the electronic module. For example, the expandable assembly can comprise two to eight splines and each of the flex-PCB substrates is attached to a different spline.

The plurality of communication paths can comprise one or more conductors comprising a material from a group comprising: copper; gold; platinum; silver; and combinations of these.

The plurality of electronic elements can comprise multiple ultrasound transducers and wherein at least one of the plurality of communication paths is electrically connected to the multiple ultrasound transducers. The at least one communication path comprise at least one coaxial cable comprising a shield and an inner conductor, and the multiple ultrasound transducers can be electrically connected to the coaxial cable shield.

The plurality of electronic elements can comprise at least one electrode and at least one ultrasound transducer, and at least one of the plurality of communication paths can be electrically connected to the at least one electrode and the at least one ultrasound transducer. The at least one communication path can comprise at least one coaxial cable comprising a shield and an inner conductor, and the at least one electrode and the at least one ultrasound transducer can be electrically connected to the coaxial cable inner conductor. The at least one communication path can comprise multiple coaxial cables each comprising a shield and an inner conductor, wherein the multiple coaxial cable shields can be electrically connected. For example, the at least one electrode can comprise a first electrode and a second electrode, and a first coaxial cable inner conductor can be electrically connected to the first electrode and a second coaxial cable inner conductor can be electrically connected to the second electrode.

The plurality of electrical contacts can be configured to be removably attached to the electronic module.

The plurality of electrical contacts can comprise an electrical connector, for example at least one of a plug or a jack.

The elongate shaft can define an elongate lumen. The lumen can extend between the shaft proximal end and distal end. The lumen can be configured to slidingly receive a guide wire and/or a shaft of a second device, for example an ablation catheter.

The shaft can comprise a steerable shaft.

The expandable assembly can be attached to the distal end of the shaft.

The shaft can comprise a distal portion, and the expandable assembly can be positioned on the shaft distal portion.

The shaft can define a lumen, and the expandable assembly can be configured to be advanced from within the lumen of the shaft.

The expandable assembly can comprise an array of splines comprising at least portions of the flex-PCB substrate. The plurality of electronic elements can be coupled to one or more splines in the array of splines. The flex-PCB substrate can have a substrate width and a first spline can have a first spline width approximately the same as the first substrate width. The flex-PCB substrate can be coupled to two or more splines from the array of splines.

The expandable assembly can comprise a plurality of splines forming a basket array or basket catheter, and the plurality of electronic elements can comprise a plurality of electrodes and a plurality of ultrasound transducers, where a plurality of electrodes and a plurality of ultrasound transducers are provided on each spline. Each spline can comprise a plurality of pairs of electrodes and ultrasound transducers, with one electrode and one ultrasound transducer per pair. The flex-PCB substrate can comprise at least one metallic layer comprising at least some of the plurality of communication paths in the form of conductive traces selectively connecting the plurality of electrodes and plurality of ultrasound transducers to connection points at proximal ends of the splines. The plurality of ultrasound transducers on each spline can share a single conductive trace. One or more wires or cables can connect the connection points to the plurality of electrical contacts.

The expandable assembly can be biased in an expanded state.

The expandable assembly can be biased in a contracted state.

The device can further comprise a handle attached to the proximal end of the shaft.

The device can further comprise a sheath with a proximal end, a distal end and a lumen therebetween, where the lumen can be constructed and arranged to slidingly receive the elongate shaft and the expandable assembly. The expandable assembly can be configured to radially expand as it exits the sheath lumen.

According to another aspect, a flex-PCB catheter configured to be inserted into a body lumen comprises an expandable assembly configured to transition from a radially compact state to a radially expanded state; a flexible printed circuit board (flex-PCB) substrate; a plurality of electronic elements coupled to the flex-PCB substrate and configured to at least one of receive or transmit an electrical signal; and a plurality of communication paths positioned at least one of on or within the flex-PCB substrate and selectively coupling the plurality of electronic elements to a plurality of electrical contacts configured to electrically connect to an electronic module configured to process the electrical signal.

According to another aspect, a method of interacting with a body via a body lumen comprises providing a device having: an elongate shaft comprising a proximal end and a distal end, an expandable assembly configured to transition from a radially compact state to a radially expanded state, a flexible printed circuit board (flex-PCB) substrate, a plurality of electronic elements coupled to the flex-PCB substrate and configured to at least one of receive or transmit an electrical signal, and a plurality of communication paths positioned at least one of on or within the flex-PCB substrate and selectively coupling the plurality of electronic elements to a plurality of electrical contacts configured to electrically connect to an electronic module configured to process the electrical signal; introducing the expandable assembly into a region of the body and expanding the expandable assembly; and supplying at least one electrical signal to the plurality of electronic elements via at least some of the plurality of communication paths. The region of the body can comprise a cardiac chamber.

In various embodiments of the method, the device can be configured and arranged in accordance with one or more of the embodiments described herein.

BRIEF DESCRIPTION OF THE DRAWINGS

The present invention will become more apparent in view of the attached drawings and accompanying detailed description. The embodiments depicted therein are provided by way of example, not by way of limitation, wherein like reference numerals refer to the same or similar elements. The drawings are not necessarily to scale, emphasis instead being placed upon illustrating aspects of the invention. In the drawings.

DETAILED DESCRIPTION OF PREFERRED EMBODIMENTS

Various exemplary embodiments will be described more fully hereinafter with reference to the accompanying drawings, in which some exemplary embodiments are shown. The present inventive concept can, however, be embodied in many different forms and should not be construed as limited to the exemplary embodiments set forth herein.

It will be understood that, although the terms first, second, etc. may be used herein to describe various elements, these elements should not be limited by these terms. These terms are used to distinguish one element from another, but not to imply a required sequence of elements. For example, a first element can be termed a second element, and, similarly, a second element can be termed a first element, without departing from the scope of the present invention. As used herein, the term "and/or" includes any and all combinations of one or more of the associated listed items.

It will be understood that when an element is referred toy as being "on" or "connected" or "coupled" to another element, it can be directly on or connected or coupled to the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, steps, operations, elements, and/or components, but do not preclude the presence or addition of one or more other features, steps, operations, elements, components, and/or groups thereof.

Spatially relative terms, such as "beneath," "below," "lower," "above," "upper" and the like may be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in the figures is turned over, elements described as "below" and/or "beneath" other elements or features would then be oriented "above" the other elements or features. The device can be otherwise oriented (e.g., rotated 90 degrees or at other orientations) and the spatially relative descriptors used herein interpreted accordingly.

Figure 1:
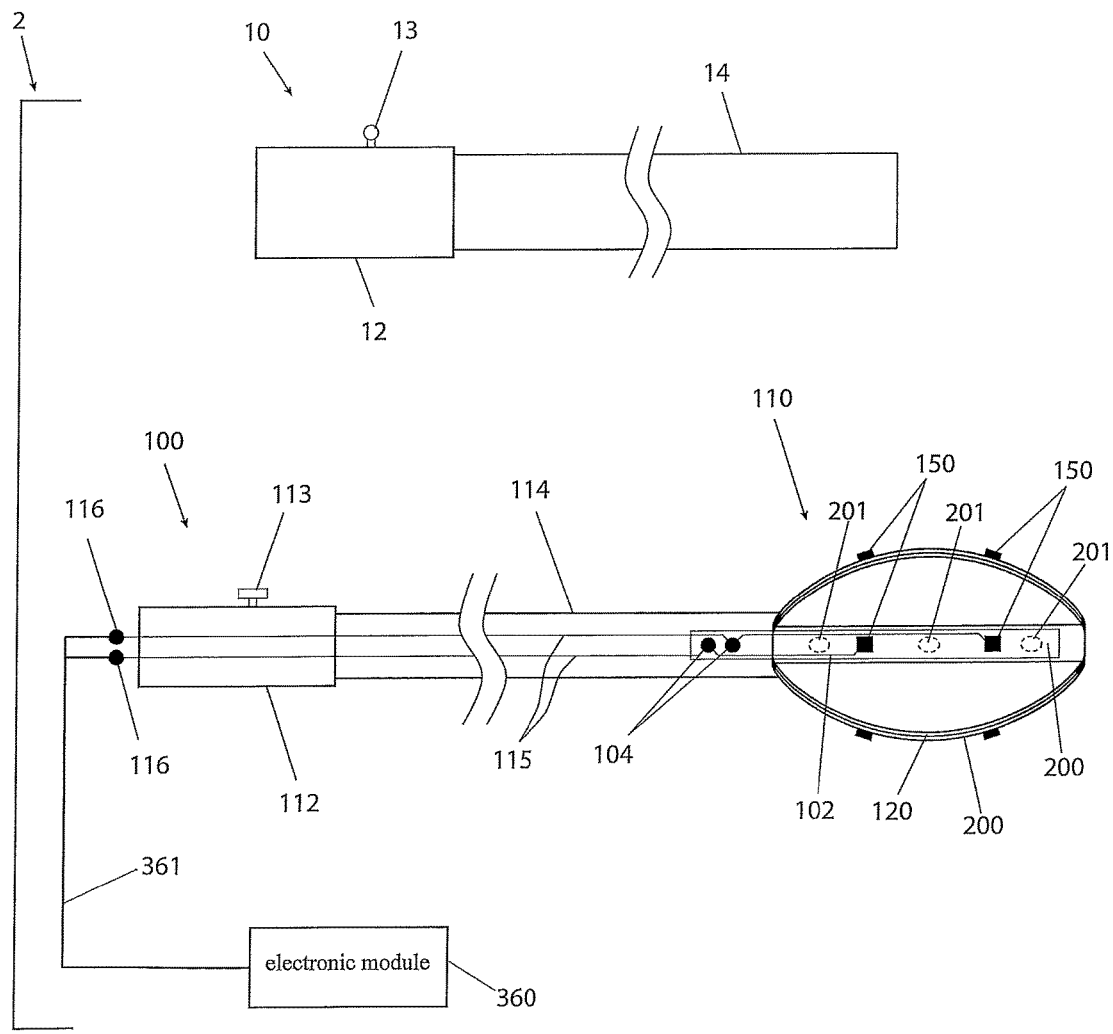
FIG. 1 is a side view of an embodiment of a catheter system comprising a flexible printed circuit board ("flex-PCB") catheter, in accordance with aspects of the inventive concepts.

FIG. 1 is a side view of an embodiment of a catheter system comprising a flexible printed circuit board ("flex-PCB") catheter, in accordance with aspects of the inventive concepts.

In the embodiment of FIG. 1, a catheter system 2 includes an introducer 10 and a flex-PCB catheter 100. In this embodiment, the introducer 10 includes a handle 12 and a shaft 14 that includes at least one lumen. In some embodiments, introducer 10 comprises a standard transseptal access sheath or other device configured to provide access to a body space such as a heart chamber. The shaft 14 is configured to slidingly receive and/or accommodate translation of the flex-PCB catheter 100 within the shaft 14. Handle 12 can include a knob, lever, switch or other control, such as control 13 that is configured to steer and/or deflect the distal end of introducer 10 and/or perform another function. In the example embodiment of FIG. 1, the handle 12, control 13, and shaft 14 are generally known in the art, so not discussed in detail herein.

The flex-PCB catheter 100 includes a handle 112 and an elongate, flexible shaft 114, extending from handle 112. Attached to the distal end of shaft 114 is a radially expandable and/or compactable assembly, expandable assembly 110. In an alternative embodiment, expandable assembly 110 is mounted to a distal portion of shaft 114, proximal to the distal end of shaft 114. In some embodiments, expandable assembly 110 is attached to shaft 114 as described in reference to applicant's co-pending U.S. Patent Application Ser. No. 61/695,535, entitled SYSTEM AND METHOD FOR DIAGNOSING AND TREATING HEART TISSUE, filed Aug. 31, 2012, which is incorporated herein by reference by its entirety. Shaft 114 and expandable assembly 110 are constructed and arranged to be inserted into a body (e.g., a human body) through a body vessel, such as a blood vessel. Such blood vessel can include a femoral vein, femoral artery, intrajugular vein, intrajugular artery, and vena cava, as examples. The expandable assembly 110 can, for example, be or include a dipole mapping device, e.g., for mapping electrical activity of the heart. In some embodiments, handle 112 includes a knob, lever, switch or other control, control 113. Control 113 can be configured to perform a function such as, for example, steering the distal end of shaft 114; controlling the expansion and/or contraction of expandable assembly 110 such as via retraction or advancement, respectively, of one or more control rods not shown, making an electrical connection such as to provide power to a component of expandable assembly 110 or electrically connecting to a sensor of expandable assembly 110, and combinations of these.

A set of one or more electrical, optical, or electro-optical wires or cables (e.g., coaxial wire or cable) 115 (collectively, "wires 115") can be provided as a communication path between the flex-PCB catheter 100 an external electrical component or system, such as electronic module 360. The wires 115 can extend through the shaft 114 to an opening in the handle 112, and terminate at one or more electrical connections (ECs) 116. The electrical connections 116 can take the form of plugs, jacks, or other connectors configured for removable attachment or coupling to electronic module 360 and/or another computer or otherwise electrically-based system, such as through electrical signal conduits 361, as shown. Such external systems can include, as examples, a power delivery system, an electrical recording system, an ultrasonic imaging or driving system, a display system, a diagnostic system, a medical treatment system, or combinations thereof, which can be user interactive.

In various embodiments, the expandable assembly 110 can be resiliently biased in a radially expanded state (e.g. a resiliently biased array of nickel titanium alloy filaments). For example, the expandable assembly 110 can be resiliently biased in a radially expanded state such that it can be radially compacted and positioned within shaft 14 and self-expand when the confinement within shaft 14 is relieved, such as when the shaft 14 is retracted relative to shaft 114 and/or when shaft 114 is advanced relative to shaft 14 such as to cause expandable assembly 110 to exit the distal end of shaft 14. In other embodiments, the expandable assembly 110 can be resiliently biased in a collapsed or radially compacted state, such as when a control rod or other mechanism is used to radially expand the expandable assembly 110.

The flex-PCB catheter 100, in this embodiment, includes a set of splines 120 that include at least one flex-PCB layer, which can be referred to as flex-PCB splines. The flex-PCB layer can be attached to a flexible filament, such as a metal (e.g. nickel titanium alloy) or plastic filament. In this embodiment, a plurality of the splines 120 have a flex-PCB configuration that includes at least one flex-PCB substrate or base layer, substrate 200 on or within which a plurality of active and/or passive electrical, optical, or electro-optical elements (EEs) 150, collectively referred to as "electronic elements 150" are provided with accompanying communication paths 102, e.g., electrical, optical, or electro-optical communication paths.

Electronic elements 150 can be configured to receive and/or transmit an electrical signal, such as an electrical signal selected from a group comprising: electrical power, an information signal, a sensor signal, a control signal, and combinations thereof. These electrical signals can be transmitted from, received by, and/or otherwise processed by electronic module 360 or other external device as described herein above. In some embodiments, electronic module 360 processing comprises a function selected from a group comprising: transmitting a power signal, transmitting a drive signal, transmitting an information signal, receiving an information signal, receiving a sensor signal, processing an information signal, analyzing an information signal, and combinations thereof.

The flex-PCB catheter 100 can include connection points 104, wherein the communication paths 102 couple the electronic elements 150 to the connection points 104 according to a specified circuit layout. In this embodiment, the wires 115 couple the connection points 104 to the external electrical connections (ECs) 116 via or within shaft 114 for connection or communication with electronic module 360. As shown in FIG. 1, connection points 104 are typically positioned within a distal portion of shaft 114.

In some embodiments, wires 115 each include a conductor surrounded by an insulator, such as a coaxial cable, which can include a shield surrounding the conductor in addition to the insulator. In some embodiments, wires 115 comprise conductive traces positioned on a flexible printed circuit board (flex-PCB) substrate, such as when substrate 200 further comprises wires 115 (e.g. when substrate 200 extends proximally through shaft 114, such as to couple electronic elements 150 to the external electrical connections 116, avoiding the need for connection points 104).

In various embodiments, the flex-PCB catheter 100 can be considered to include the expandable assembly 110, comprising the electronic elements 150, formed at a distal end and the connection points 104 formed at a proximal end (near or within shaft 114). The expandable assembly 110 can, in some embodiments, take to the form of an array, such as a basket array, as in FIG. 1. In such cases, the expandable assembly 110 can be referred to as a flex-PCB basket catheter. The basket array can be configured to have the above-mentioned biasing in an expanded or collapsed state, such as an array of nickel-titanium or other flexible splines one or more of which includes a flex-PCB attached thereto. Flex-PCB substrate 200 can be attached to expandable assembly 110 with an attachment element 201, such as an adhesive, a clip, a crimp, at attachment element or the like. In some embodiments, flex-PCB substrate 200 is continually attached along a length of one or more splines 120. Alternatively or additionally, flex-PCB substrate 200 can be attached along a length of one or more splines 120 with one or more attachment elements 201 positioned at one or more discrete attachment locations (as shown in FIG. 1), such as to allow independent flexing of flex-PCB substrate 200 and splines 120 alongside or in-between the one or more attachment elements 201 (e.g. bending at an unattached segment allows relative movement between flex-PCB substrate and spline 120 at that segment, decreasing the rigidity of expandable assembly 110 when flex-PCB substrate 200 is attached).

In various embodiments, the splines 120 can have the same length or different lengths. And in some embodiments, the connection points 104 on different splines 120 can be staggered to accommodate a tight collapsed or contracted configuration of the expandable assembly 110, as will be discussed below.

In various embodiments, the electronic elements 150 can include more than one type of electrical, optical, or electro-optical components. Therefore, different types of electrical components can be included on or in one or more splines 120 to accommodate one or more active and/or passive functions. In some embodiments, different splines 120 can include different numbers, types, and/or arrangements of electronic elements 150.

As examples, types of electronic elements 150 can include, but are not limited to, electrodes, transducers, accelerometers, sensors, integrated circuits (e.g., semiconductors), and so on. As examples, such sensors can include, but are not limited to, temperature sensors, pressure sensors (e.g., strain gauges), voltage sensors, current sensors, acoustic sensors, and so on. As examples, such transducers can include, but are not limited to, ultrasound transducers, sound transducers, heating elements, cooling elements, and so on. The integrated circuits could include, but are not limited to, multiplexers (MUX), demultiplexers (DEMUX), A/D converters, D/A converters, electrical/optical converters, optical/electrical converters, analog or digital signal filters (or other filters), amplifiers, pre-amplifiers, transducers, combinations thereof, and so on. For instance, a MUX can be used to reduce the number of wires to the expandable assembly 110. An A/D converter could be used to reduce wires and/or reduce or eliminate noise susceptibility such as to avoid a need for coax cables. An amplifier can be used to boost one or more signals.

Figure 2A:
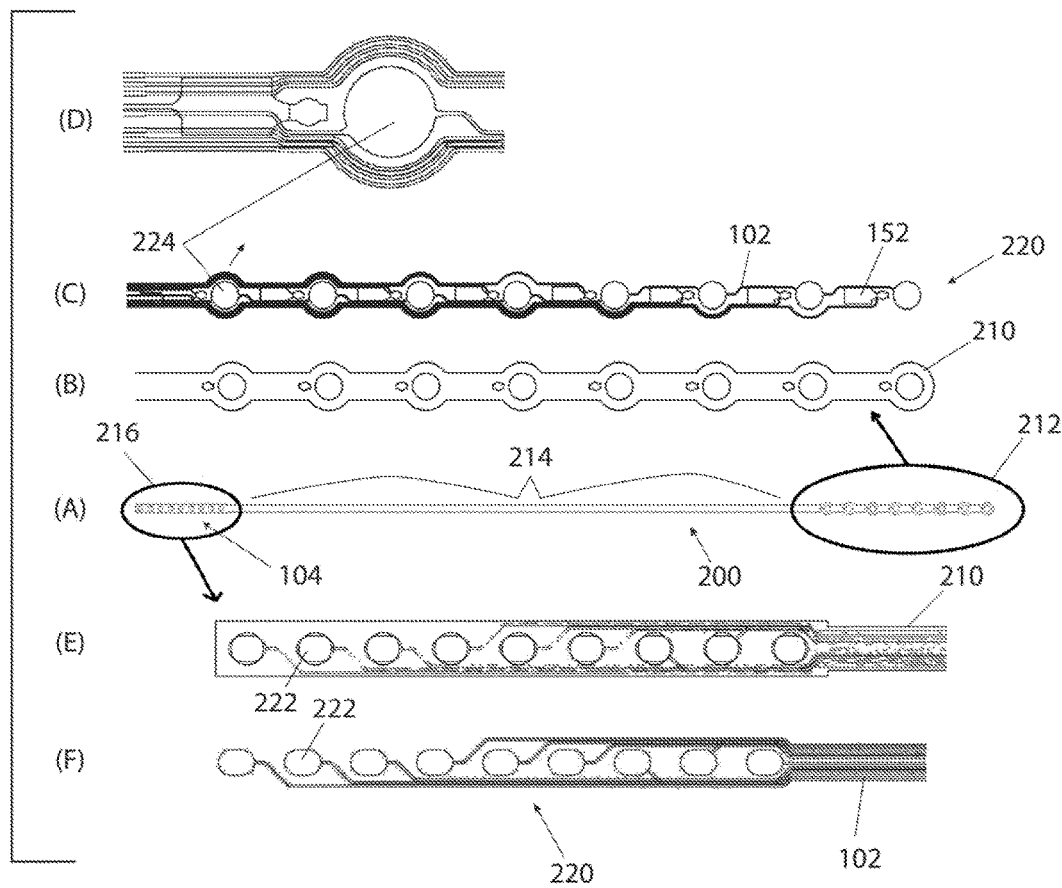
FIGS. 2A and 2B provide bottom and top views of portions of an embodiment of a flexible printed circuit board ("flex PCB") that can comprise an expandable assembly, in accordance with aspects of the inventive concepts.
Figure 2B:
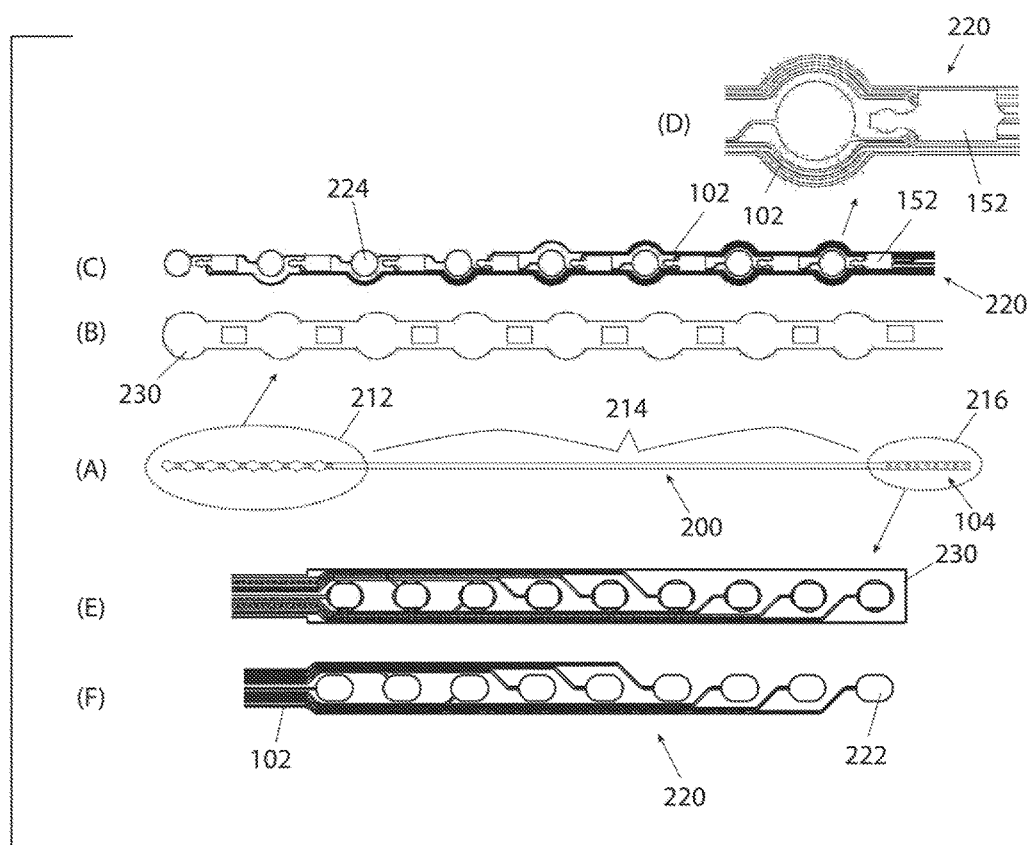

FIGS. 2A and 2B provide bottom and top views, respectively, of portions of an embodiment of a flex-PCB substrate 200 that forms part of the spline 120 of the expandable assembly 110 of FIG. 1, in accordance with aspects of the inventive concepts. For the purposes of this description, the bottom view is a perspective from within the expandable assembly 110 and the top view is a perspective from outside the expandable assembly 110. Each of the splines 120 includes a span or length 214 between the electrode regions 212 and connection portion 216.

In various embodiments, the flex-PCB substrate 200 can include a single layer or a multilayer flex-PCB, each of which can comprise electrical pathways on one or both sides (i.e. single sided or double sided). In the embodiment of FIGS. 2A and 2B, the flex-PCB substrate 200 has a multilayer construction, where the layers are laminated together, with the flex-PCB substrate comprising the connection points 104 and communication paths 102, and supporting the electronic elements 150. The communication paths 102 and connection points 104 can be formed on either or both sides of, or within, the flex-PCB substrate 200, or combinations thereof. Similarly, the electronic elements 150 can be mounted on either or both sides of, or disposed within, the flex-PCB substrate 200, or combinations thereof.

In this embodiment, the electronic elements 150 are arranged at the distal end of the flex-PCB substrate 200 in an electrode region 212 and the connection points 104 are arranged at the proximal end of the flex-PCB substrate 200 in a connection portion 216, with the communication paths 102 coupling specific connection points 104 with specific electronic elements 150 across a span or length 214 of the flex-PCB substrate 200.

FIG. 2A shows a bottom view of the flex-PCB substrate 200. Part (A) shows a substantially complete bottom view of the flex-PCB substrate 200. Part (B) shows a view of the electrode region 212 of the flex-PCB substrate 200, comprising portions of a bottom cover layer 210 and portions of a metallic layer 220 forming part of the expandable assembly 110. Part (C) shows a view of the metallic layer 220 from Part (B) in the electrode region 212. Part (D) shows a view of a portion of the metallic layer 220 from Part (C). Part (E) shows a view of the connection portion 216 of the flex-PCB substrate 200, comprising portions of the bottom cover layer 210 and portions of the metallic layer 220 forming part of the connection points 104 in the connection portion 216. And part (F) shows a view of the metallic layer 220 from Part (E).

In the bottom view of FIG. 2A, the flex-PCB substrate includes the bottom cover layer 210 and the metal or metallic layer 220 that is disposed on the bottom cover layer 210. In the embodiment of FIGS. 2A and 2B, the communication paths 102 take the form of one or more conductive traces of the metallic layer 220 formed on or within the flex-PCB substrate 200.

In the connection portion 216 of the flex-PCB substrate 200, the metallic layer 220 includes metallic pads 222 provided in the form of vias (pathways which provide an electrical connection from one side of a layer to the opposite side), which comprise the connection points 104. That is, openings are formed in the bottom cover layer 210 to expose the pads 222, as the connection points 104.

In the electrode region 212 of the of the metallic layer 220, having the expandable assembly 110, metallic pads 224 are provided as bases for at least some of a first set of the electronic elements 150. For example, in this embodiment, the metallic pads 224 can be piezoelectric transducer (PZT) pads used to support one or more ultrasound elements (not shown). Openings are formed in the bottom cover layer 210 to expose the metallic pads 224. Between the metallic pads 224, also as part of the metallic layer 220, a second set of electronic elements 150 can be provided, e.g., in the form of electrodes 152. In this embodiment, the electrodes 152 are provided between metallic pads 224, and ultimately between individual ones of the first set of electronic elements (e.g., ultrasound crystals) mounted on the metallic pads 224.

FIG. 2B shows a top view of the flex-PCB substrate 200. Part (A) shows a substantially complete top view of the flex-PCB substrate 200. Part (B) shows a view of the electrode region 212 of the flex-PCB substrate 200, comprising portions of a top cover layer 230 and portions of the metallic layer 220 forming part of the expandable assembly 110. Part (C) shows a view of the metallic layer 220 from Part (B). Part (D) shows a view of a portion of the metallic layer 220 from Part (C). Part (E) shows a view of the connection portion 216 of the flex-PCB substrate 200, comprising portions of the top cover layer 230 and portions of the metallic layer 220 forming part of the connection points 104. And part (F) shows a view of the metallic layer 220 from Part (E).

In the embodiment of FIG. 2B, there is shown the top cover layer 230 and the metallic layer 220. The top cover layer 230 is combined with the bottom cover layer 210, with the metallic layer 220 maintained between the bottom and top cover layers 210 and 230 respectively. In this embodiment, the top cover layer 230 substantially covers the communication paths 102 of the flex-PCB substrate 200. The top cover layer 230 also covers the metallic pads 224 which are constructed and arranged to provide acoustic matching in the expandable assembly 110 portion of the spline 120. Ultrasound crystals, as an example, can later be mounted on the top cover layer 230 and the metallic pads 224, as will be discussed below. The electrodes 152 can also be mounted on the top cover layer 230 and connect to the metallic layer 220 through the top cover layer 230.

In the connection portion 216 of the flex-PCB spline 120 openings are formed in the top cover layer 230 to expose the pads 222, as the connection points 104.

In the metallic layer 220, traces and pads can be made of electrically conductive materials that can be formed by laser cutting, chemical etching, molding or casting, and/or by printing, as examples. The bottom cover layer 210 can be laser cut and laminated to the metallic layer 220 or the metallic layer 220 can be deposited and etched directly to the bottom cover layer 210, in various embodiments. The top cover layer 230 can be laminated onto the bottom cover layer 210, with the metallic layer 220 in between.

In the embodiment of FIGS. 2A and 2B, the flex-PCB substrate 200 supports eight (8) sets of electronic elements 150 (e.g. 16 components) for a given spline 120. In other embodiments, a different number of sets of electronic elements 150 could be used, e.g., 2, 4, or 6 sets of electronic elements per spline 120. In the present example embodiment, each set of electronic elements 150 includes one electrode 152 and one corresponding ultrasound transducer coupled to one corresponding metallic pad 224. The electrodes 152 can comprise one or more coatings, such as a coating constructed and arranged to reduce impedance at one or more ranges of frequencies, as an example. The ultrasound transducers, as an example, can be mounted to the flex-PCB substrate 200 in any of a variety of ways, e.g., they can be contained within cups or a housing, in some embodiments. (See, e.g., FIG. 8.)

In various embodiments, the metallic pads 224 of the metallic layer 220 can serve as an acoustic matching layer that maximizes the power transfer and efficiency of a corresponding transducer (e.g., an ultrasound transducer). The metallic pads 224 are specifically configured to match the acoustic impedance of the transducer material (e.g., PZT) to that of the propagating medium (water, blood, etc.).

Optimal impedance matching is achieved when the matching layer thickness is a quarter (¼) wavelength at an operating frequency within that material when the acoustic impedance is given by Z_match=sqrt (Z_transducer*Z_media). It can be difficult to find or engineer a material to have the exact acoustic impedance for a quarter-wave matching layer, thus, the thickness and acoustic impedance can be varied in order to minimize losses. Composite or multi-layer materials can be used for matching layers, in various embodiments. The loss due to impedance mismatch of the matching layer can be calculated or simulated, and the particulars of the metallic pads 224 determined therefrom.

In the present embodiment, the flex-PCB substrate 200 can be configured as, or to include, a matching layer—as part of metallic layer 220. For example, a polyimide layer of the flex-PCB substrate can be configured with an acoustic impedance that can be used as a matching layer when the thicknesses of the bonding adhesive, metallized electrode, and substrate layers are controlled. The thickness of each of these layers in the flex-PCB substrate 200 design is selected to balance the tradeoffs of acoustic and electrical performance, as well as the availability and/or cost of materials.

The bottom cover layer (or backing layer) 210 also affects the power transfer efficiency and bandwidth of the transducer mounted on the flex-PCB substrate 200. The bottom cover layer 210 is selected to minimize the energy transmitted out of the back of the transducer, while also attenuating any acoustic energy that does enter the bottom cover layer 210 (e.g. to increase the transducer bandwidth).

The electrodes 152 can be deposited directly on the bottom cover layer 210, e.g. via electro-deposition, ion beam deposition, sputtering, and combinations thereof. As an alternative to the deposition on the bottom cover layer 210, the electrodes 152 can be mounted to the flex-PCB substrate 200 (e.g. with an adhesive such as an insulating glue), then electrically connected to communication paths 102 within the flex-PCB substrate 200. In various embodiments, the electrodes 152 can be formed from copper, gold, platinum, iridium, stainless steel and/or other conductive materials or elements. The electrodes 152 can optionally be coated with a surface coating, such as iridium oxide, platinum black (Pt black), PEDOT (i.e., poly(3,4-ethylenedioxythiophene)), or carbon nanotubes, as examples.

In various embodiments, the communication paths 102 can be traces within or on the flex-PCB substrate formed of copper, gold, platinum, or silver, as examples. In various embodiments, the matching layer metallic pads 224 can be formed of copper, gold, platinum, or silver, as examples. And in various embodiments, the bottom and top cover layers, 210 and 230 respectively, can be formed of polyimide, polyester, nylon, polyether block amide (PEBA or PEBAX), liquid crystal polymer (LCP), and so on.

Figure 3A:
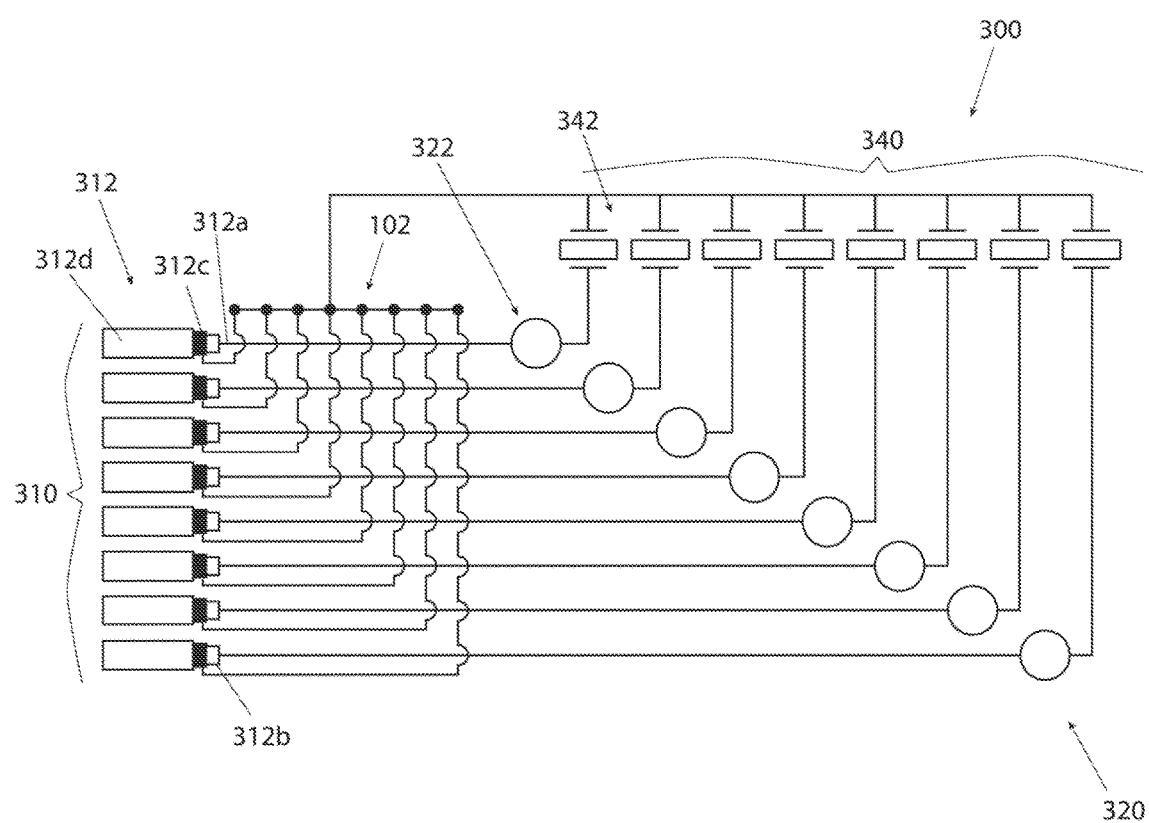
FIGS. 3A and 3B provide schematic diagrams showing an embodiment of an electrical layout of the flex-PCB catheter and related apparatuses of FIGS. 2A and 2B, in accordance with aspects of the inventive concepts.
Figure 3B:
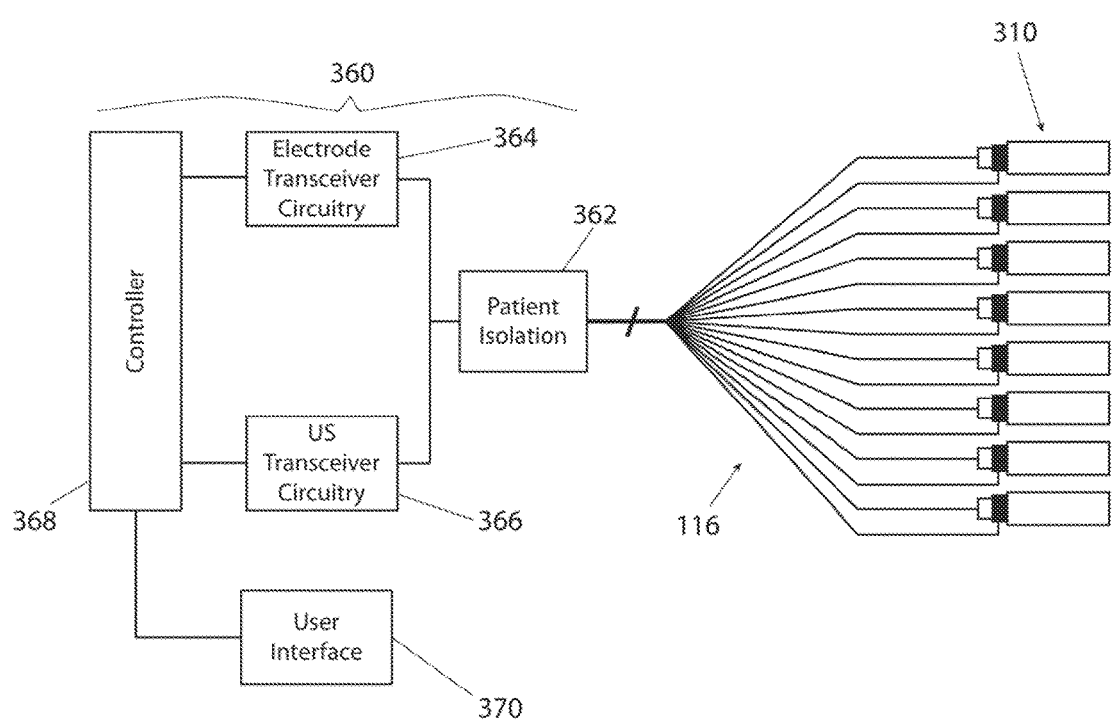

FIGS. 3A and 3B provide schematic diagrams showing an embodiment of an electrical layout 300 of the flex-PCB catheter 100 of FIGS. 1, 2A and 2B connected to a set of corresponding coaxial cables 310 (as an example of wires 115), in accordance with aspects of the inventive concepts. FIG. 3A represents a schematic of an embodiment of connections of the coaxial cables 310 to the flex-PCB catheter 100. FIG. 3B represents a schematic of an embodiment of connections of the coaxial cables 310 to at least one external system, electronic module 360, via the electrical connections 116.

The electrical layout 300 shows the coaxial cables 310 comprising eight (8) coax cables, including coax cable 312, coupled to respective eight (8) electrodes 320, including electrode 322, which can be equivalent to the electrodes 152, and to eight (8) ultrasound transducers 340, including ultrasound transducer 342. These elements, along with the communication paths 102 (e.g., conductive traces), are shown in schematic form in FIG. 3A.

Coax cable 312, as an example, includes an inner conductor 312a, an insulator 312b, a shield 312c, and a casing 312d. The inner conductor 312a of coax cable 312 couples to the electrode 322 and then to a terminal of the ultrasound transducer 342. A second terminal of the ultrasound transducer 342 couples to the shield 312c of coax cable 312. In this embodiment, the second terminals of the ultrasound transducers 340 can share a common wire or trace, as a manner of being commonly connected. The shields of all of the coax cables 310 are also commonly connected. In other embodiments, the second terminals of the ultrasound transducers 340 and/or shields need not be commonly connected, or different sets of the second terminals of the ultrasound transducers 340 and/or the shields can be commonly connected. In some embodiments, coax cables 310 comprise an electrical characteristic selected from a group comprising: an approximate capacitance of 115 pF/meter at 1 kHz; a characteristic impedance between 75Ω and 1000Ω; a characteristic impedance of approximately 200Ω; an attenuation of between 0.3 dB/meter and 1.0 dB/meter at 10 MHz; an attenuation of approximately 0.5 dB/meter at 10 MHz; and combinations of these.

The other coax cables 310 can have the same configuration and arrangement with their respective electrodes 320 and ultrasound transducers 340.

In the embodiment of FIG. 3B, the coax cables 310 are coupled to electronic module 360. In this embodiment, the electronic module 360 includes a patient isolation circuit 362, an electrode transceiver circuit 364, ultrasound transceiver circuit 366, a controller 368, and a user interface 370. The foregoing circuits can, as an example, form or be part of an external system that provides cardiac activity analysis, mapping (e.g. recording and/or analysis of recorded electrical signals), treatment (e.g. providing ablative energy), or some combination thereof.

In the embodiment shown in the high-level schematic of FIG. 3B, the electrode circuitry, ultrasound circuitry, user interface, and controller are electrically isolated from the patient (e.g. to prevent undesired delivery of a shock or other undesired electrical energy to the patient), via the patient isolation circuit 362, which can form part of electronic module 360 or can be separate therefrom.

Figure 4:
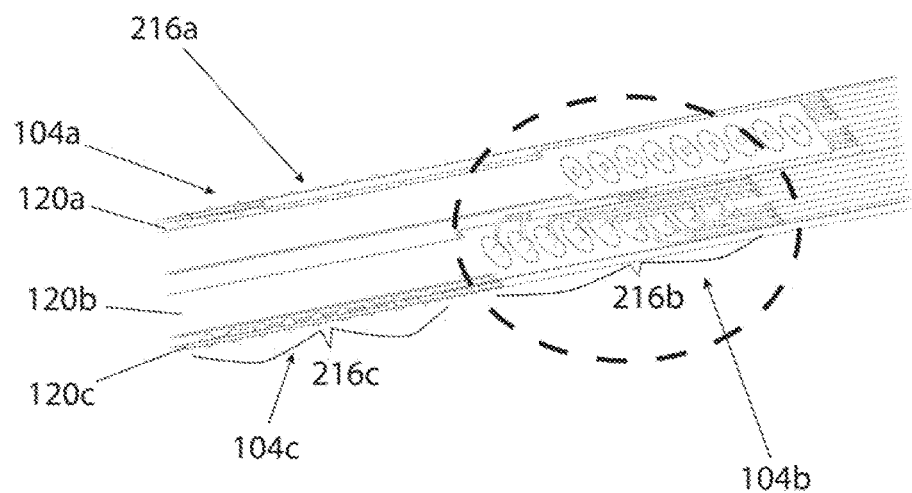
FIG. 4 is a perspective view of an embodiment of proximal ends of flex-PCB splines having staggered connection portions, in accordance with aspects of the inventive concepts.
Figure 4:
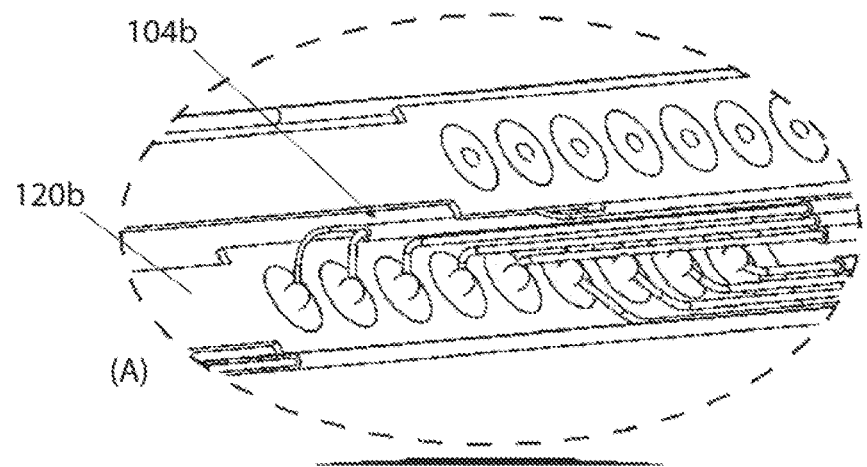

FIG. 4 is a perspective view of an embodiment of the connection portions 216 (i.e., proximal ends) of the splines 120 of an expandable assembly 110, in accordance with aspects of the inventive concepts. In this embodiment, the splines 120 have linearly staggered connection portions 216a, 216b and 216c (generally 216), and each connection portion 216 has a set of linear staggered connection points 104a, 104b and 104c (generally 104), respectively. Generally, the connection portions 216 are on a portion of the flex-PCB catheter 100 that is contained within a distal portion of a shaft, such as shaft 114 of FIG. 1. Linear staggering of connection portions 216, and/or the linear staggering of connections points 104 allows an efficiently radially compact design of a surrounding shaft, and/or a shaft through which the connection portions 216 will be advanced through (e.g. shaft 14 of FIG. 1). In this embodiment, the proximal ends connection portions 216a, 216b, and 216c are staggered with respect to their locations on their respective splines 120a, 120b, and 120c. Thus, the corresponding connection portions 216a, 216b, and 216c (and connection points 104a, 104b, and 104c) of at least two splines 120a, 120b, and/or 120c, are not directly adjacent and side-by-side to each other—they are offset or staggered. This can be the case for some or all of the splines 120 forming the flex-PCB catheter 100.

In FIG. 4, the splines 120 are shown having different lengths, but in other embodiments the splines could be substantially the same length, with their connection portions at different locations on the splines. Thus, the connection portions would remain offset or staggered, even if the splines 120 are substantially the same length, and allow efficient radially compacting of splines 120 due to the staggered positioning.

FIG. 4 further includes a callout (A) that shows an embodiment of an arrangement of connections 104b in the connection portion 216b for spline 120b. In this embodiment, nine connections are shown for spline 120b, in a linearly staggered arrangement as described above. Eight (8) connections are provided to eight (8) conductors via the flex-PCB substrate 200, such as the inner conductor 312a of coax cable 312 in FIGS. 3A and 3B. A ninth connection is also provided to a shield as a wire or trace shared by the eight (8) transducers on spline 120b, e.g., see transducers 340 and shield 312c of coax cable 312 in FIG. 3A). In this embodiment, the right-most connection is connected to the shield, but in other embodiments this need not be the case. This arrangement of connections can also be provided for one or more other splines in the expandable assembly 110.

In this embodiment, the conductors (or wires) can be laser welded, bonded with conductive adhesive, or soldered to respective vias (see, e.g., pads 222 in FIGS. 2A and 2B). Each connection can have a vertical dimension (i.e., depth and/or height). Staggering connection portions alleviates congestion caused by the vertical dimensions of the connections, and the connection portions 216 generally, allowing an efficient, radially compact configuration of the portions of the device including the connection points 104.

Figure 5:
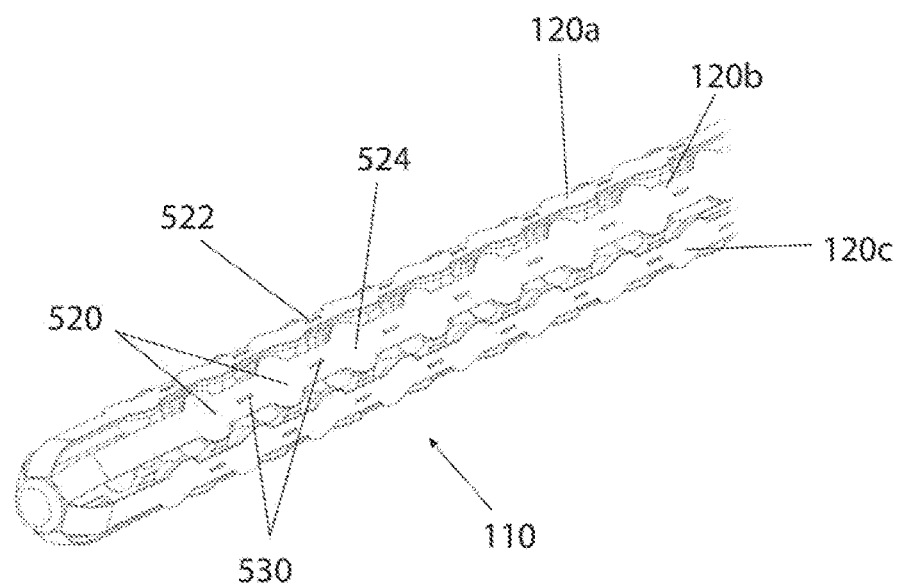
FIG. 5 is a perspective view of an embodiment of a portion of an expandable assembly in a collapsed state, in accordance with aspects of the inventive concepts.

FIG. 5 is a perspective view of an embodiment of a portion of an expandable assembly 110 in a collapsed state, in accordance with aspects of the present invention. In FIG. 5, a backing layer is externally visible, such as the top cover layer 230 shown in FIG. 2B.

In this embodiment, the expandable assembly 110 includes six (6) splines 120, including splines 120a, 120b, and 120c. Each of the splines 120 includes a plurality of first electronic element locations 520 and a plurality of second electronic element locations 530. Thus, two or more types of electronic elements 150 can be included in each spline 120. As examples, the first electronic element locations 520 can include or accommodate ultrasound transducers, e.g. transducer 524, and the second electronic element locations 530 can include or accommodate electrodes, e.g., electrode 522.

In this embodiment, the first electronic element locations 520 are wider than adjacent and/or intermediate regions of the splines 120, and the second electronic element locations 530, and are generally circular. In other embodiments, the first electronic element locations 520 could have different shapes. To facilitate a more compact arrangement of the expandable assembly 110 and the splines 120, the first electronic element locations 520 are staggered or offset from spline to spline. Therefore, a protrusion of one first electronic element location 520 on spline 120a can be located between two protrusions of neighboring first electronic element locations 520 on neighboring spline 120b, as an example. This staggered arrangement can be provided for all of the splines 120.

The embodiment of FIG. 5 shows substantially straight splines 120 with laterally protruding first electronic element locations 520. In other embodiments, the splines 120 need not be substantially straight. For example, the splines 120 could have plural curved sections (e.g., a sinusoidal wave shape), a saw tooth or zigzag shape, a square wave shape, or some other shape that could create a staggered or interleaved arrangement of the expanded assembly 110 in the collapsed state. In such cases, the first electronic element locations 520 need not have lateral protrusions on one or both sides of the splines.

Figure 6:
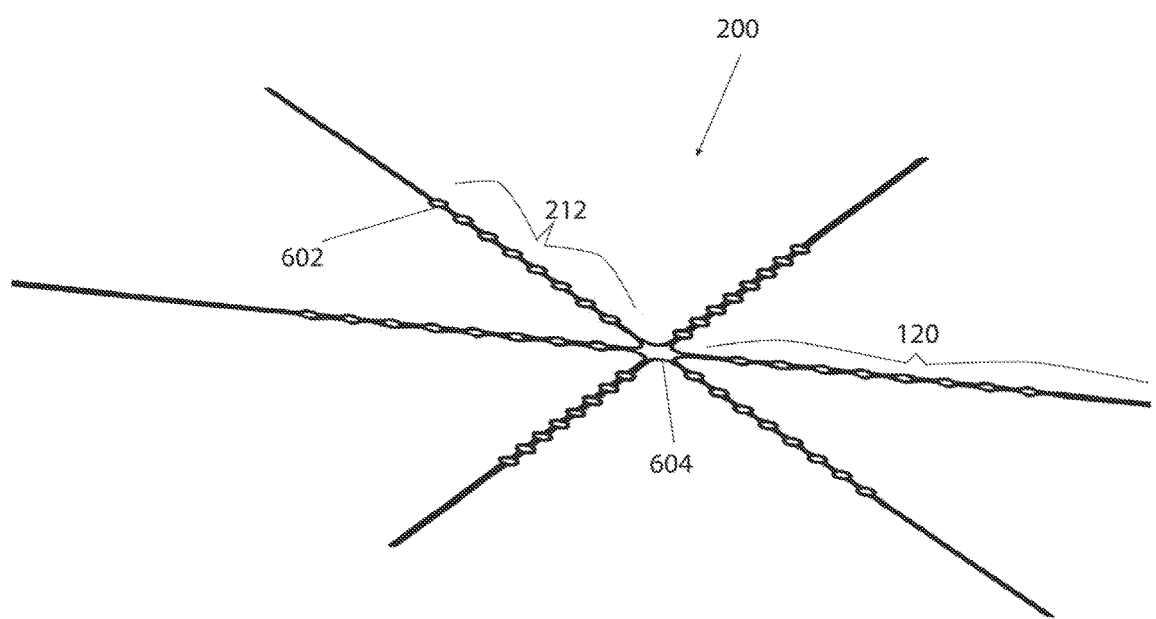
FIG. 6 is a perspective view of an embodiment of a flex-PCB layer of a flex-PCB expandable assembly, in accordance with aspects of the inventive concepts.

FIG. 6 is a perspective view of an embodiment of a flex-PCB substrate 200 of the flex-PCB catheter 100 (e.g., a basket catheter), in accordance with aspects of the inventive concepts. In this embodiment, the flex-PCB substrate 200 is configured to accommodate six splines 120. Each spline 120 defines a plurality of openings 602 in the electrode regions 212 to accommodate mounting of a plurality of electronic elements, such as ultrasound crystals as an example or other electronic elements 150 described in FIG. 1.

The flex-PCB substrate 200 defines a central opening 604. The opening 604 could accommodate passage of a guidewire and/or a second catheter, e.g., an ablation catheter, in some embodiments, described further in FIG. 10.

The flex-PCB substrate 200 can be a single or multi-layer flex-PCB layer made as a single work piece. For example, the flex-PCB substrate 200 could be laser cut from a single piece of flex-PCB material. As such, manufacturing complexity and time, and cost can be reduced.

Also, in this embodiment, the splines 120 have various lengths so that the connection portions can be staggered, as discussed above. But this need not be the case in all embodiments. In some embodiment, the splines 120 can be substantially the same length.

Figure 7A:
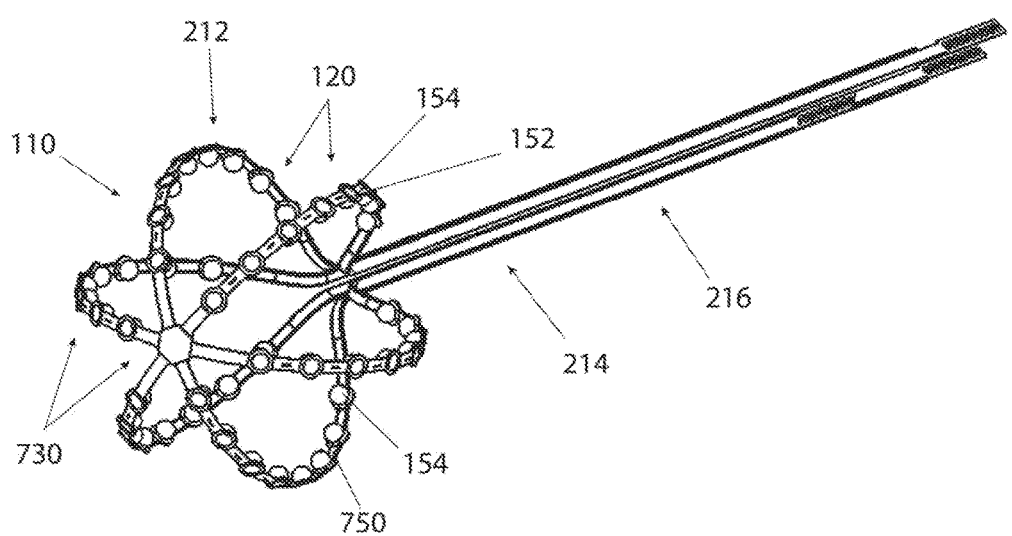
FIGS. 7A and 7B are perspective views of an embodiment of a flex-PCB catheter and portions thereof, in accordance with aspects of the inventive concepts.
Figure 7B:
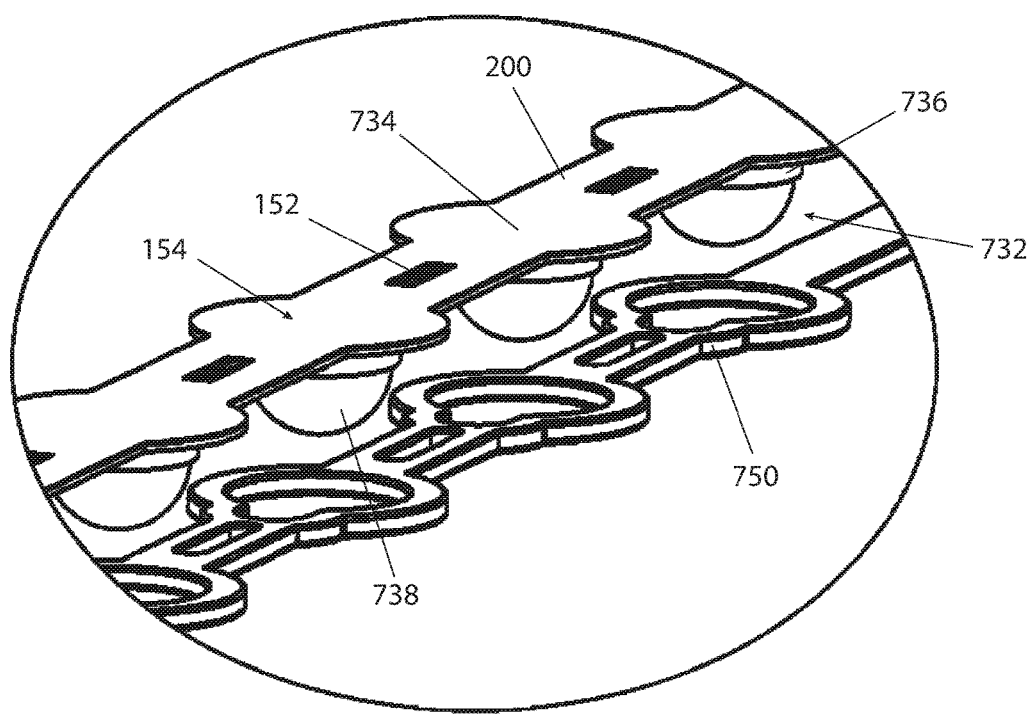

FIGS. 7A-7B are perspective views of embodiments of a flex-PCB catheter and portions thereof, in accordance with aspects of the inventive concepts. The flex-PCB catheter can take the form of the flex-PCB catheter 100 of FIGS. 1, 2A and 2B, as an example.

In the embodiment of FIG. 7A, the flex-PCB catheter 100 includes the expandable assembly 110 (e.g., basket catheter) comprising six splines 120. Each spline includes eight sets 730 of electronic elements 150, each set 730 comprising an ultrasound transducer 154 and an electrode 152. In other embodiments, more or less splines could be provided, with different numbers of electronic elements 150 and/or electronic element sets 730.

Each of the splines 120 includes a span or length 214 between the electrode regions 212 and connection portion 216, as described with respect to FIGS. 2A, 2B and 4. In an embodiment, the spans 214 and connection portions 216 are maintained within a shaft (e.g. shaft 114 of FIG. 1), in both the expanded state (as shown) and the collapsed state of the expandable assembly 110. Also, in this embodiment, the splines 120 have various lengths so that the connection portions 216 are linearly staggered, minimizing the required diameter of shaft 114, as discussed above in relation to FIG. 4.

Referring to FIG. 7B, in this embodiment, the ultrasound transducer 154 is of the immersion type, since it can be immersed in blood within the heart, in the example embodiment. The ultrasound transducer 154 comprises an acoustic matching layer 734, an active element (e.g., a PZT pad or electrode) 736, and a backing material (or cover) 738.

The flex-PCB catheter 100 of FIG. 7B includes the flex-PCB substrate 200 having defined openings that are occupied by acoustic matching (or balancing) pads 732. As an example, the acoustic matching pad 732 can be soldered or glued into place. The active element 736 can be mounted on the acoustic matching pad 732, and the backing material 738 can be disposed on the active element 736, as is shown.

In FIGS. 7A and 7B a spline support 750 is shown that can assist in giving shape and/or shape biasing to the expandable assembly 110.

Figure 7C:
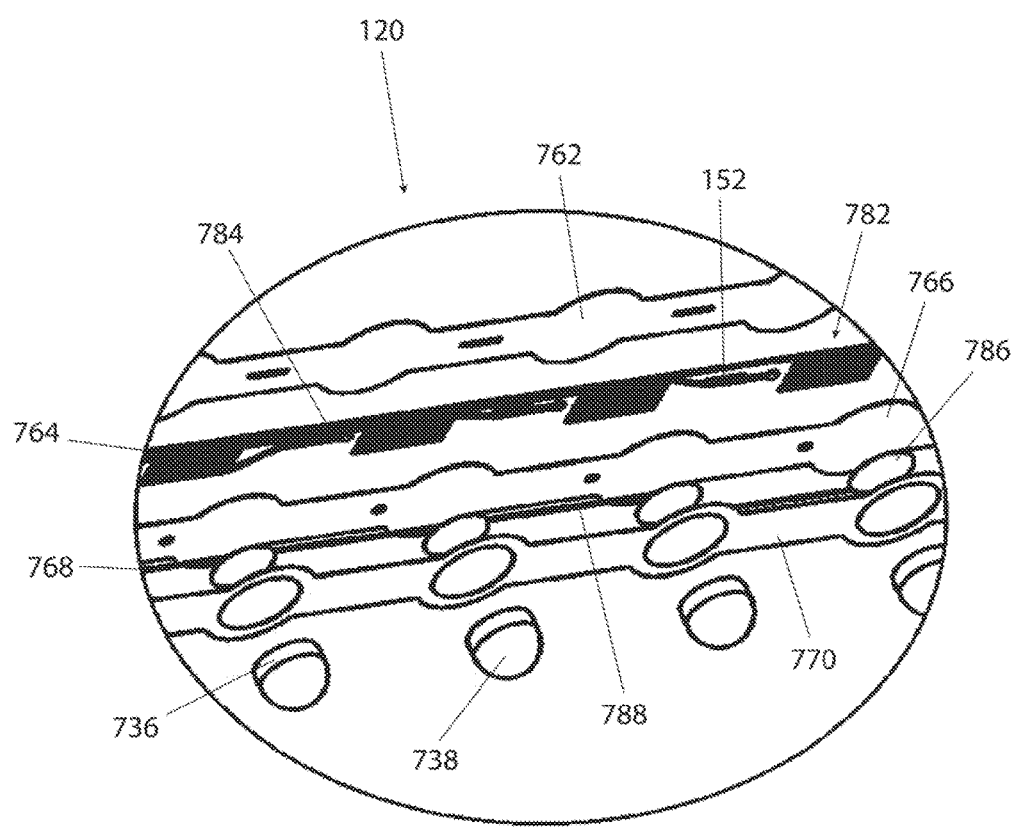
FIG. 7C shows an exploded view of an embodiment of a multi-layer spline, in accordance with aspects of the inventive concepts.

FIG. 7C shows an exploded view of embodiment of a multi-layer spline, in accordance with aspects of the inventive concepts. The spline of FIG. 7C can be an embodiment of spline 120.

The portion of spline 120 in FIG. 7C comprises a first laminate layer 762 (e.g., top cover layer 230 of FIG. 2B), a first metallic layer 764, a second laminate layer 766, a second metallic layer 768, a third laminate layer 770 (e.g., bottom cover layer 210 of FIG. 2A), active elements (e.g., PZT) 736, and backing material 738. The layers 762, 764, 766, 768, and 770 can be laminated together to form an embodiment of the flex-PCB substrate 200.

In this embodiment, the first metallic layer 764 includes electrodes 152, forming part of electronic element sets 730, balance traces 782 disposed beneath the active elements 736, and an electrode trace 784 that connects the electrodes 152. In the embodiment of FIG. 7C, each active element 736 has the same amount of balance pad (or trace) 782 "underneath" it, which is different from the embodiment of FIGS. 2A and 2B, where traces do not travel "beneath," but around the metallic (e.g., PZT) pads 224. In this configuration, balance traces 782 are positioned beneath each element 736 and are configured to acoustically balance each element 736. In some embodiments, balance traces 782 do not carry an electrical signal (i.e. traces 782 are not electrically connected to any other electronic component or conductive trace). For example, along a spline 120, the area beneath each active element 736 can include a set of electrical traces including one or more electrode traces 784 and zero or more balance traces 782. To achieve an acoustic or other mechanical balance, the total number of traces is the same quantity beneath each active element 736. For example, in a spline containing eight active elements 736, the most proximal active element 736 will have eight electrode traces 784 and zero balance traces 782 positioned beneath it, each successive more distal active element 736 will have one less electrode trace 784 and one more balance trace 782 positioned beneath it (as compared to the active element 736 just proximal to that active element 736), incrementally continuing to the most distal active element 736 which has one electrode trace 784 and seven balance traces 782 beneath it. In alternative embodiments, electrode traces 784 can be positioned in an area not beneath each active element 736, such as to avoid the need for balance traces 782 as is shown in FIG. 2A.

In this embodiment, the second metallic layer 768 is an ultrasound transducer trace that includes pads 786 on which the active elements 736 are mounted. The pads are electrically connected with trace lines 788. The various traces provided in the first and second metallic layers 764, 768 can be configured to accomplish the connections shown in the schematic diagram of FIG. 3A.

Figure 8:
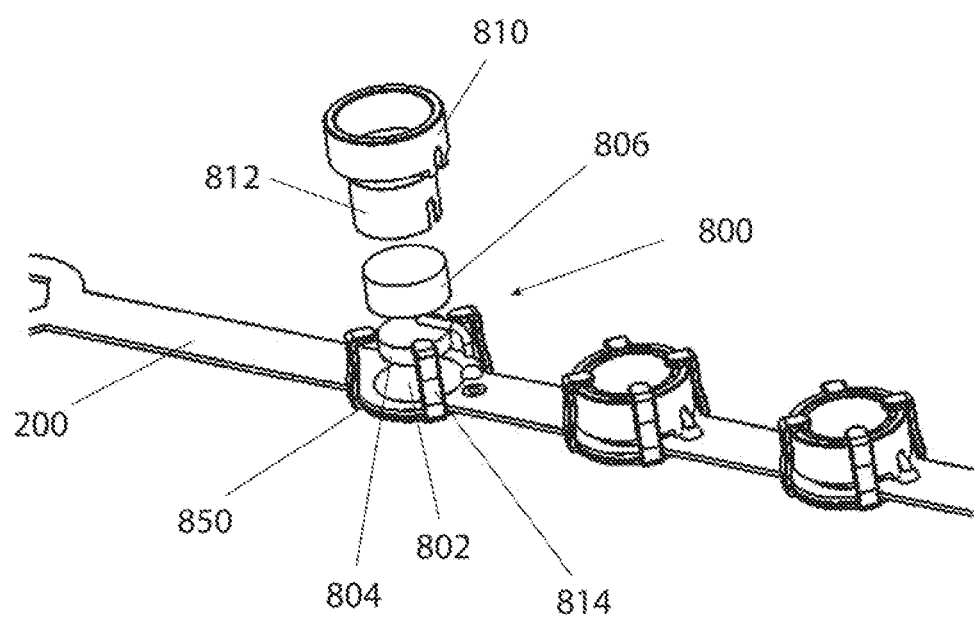
FIG. 8 shows a portion of another embodiment of a spline of a flex-PCB catheter, in accordance with aspects of the inventive concepts.

FIG. 8 shows a portion of another embodiment of a spline of a flex-PCB catheter, in accordance with aspects of the inventive concepts. In various embodiments, that is, spline 120 can take the form shown in FIG. 8.

In the embodiment of FIG. 8, an embodiment of the flex-PCB substrate 200 is shown with a plurality of ultrasound transducers 800 mounted thereon. In this embodiment, ultrasound transducer 800 includes a matching material 802 within the flex-PCB substrate 200 and an active element (e.g., a PZT pad) 804 on the matching material 802 and a backing material 806 on the active element 804.

In FIG. 8, the flex-PCB substrate 200 can be substantially covered by a spline support 850, which can be attached to the flex-PCB substrate 200 in one or more locations. The location can be discrete, non-continuous locations—e.g. including an unfixed portion to allow relative motion between, to avoid the spline 120 from becoming stiff.

The ultrasound transducer 800 can be attached to the spline support 850 and/or flex-PCB substrate 200 with adhesive, crimp, and/or housing that surrounds (captures) ultrasound transducer 800. In this embodiment, the ultrasound transducer 800 is coupled to the spline 120 using a housing 810. The housing 810 can include an inner housing component 812, and the two can substantially surround and secure the ultrasound transducer 800. The housing 810 can be coupled or secured to the spline 120 via any or a variety of securing mechanisms. In FIG. 8, the housing 810 is secured to spline 120 using one or more clips 814.

A benefit of the two piece protective cups, i.e., housing 810 and inner housing component 812, is to secure the ultrasound transducers 800 to the array and to protect the flex-PCB substrate to active element 804 (e.g., PZT) bond from side loads.

Figure 9A:
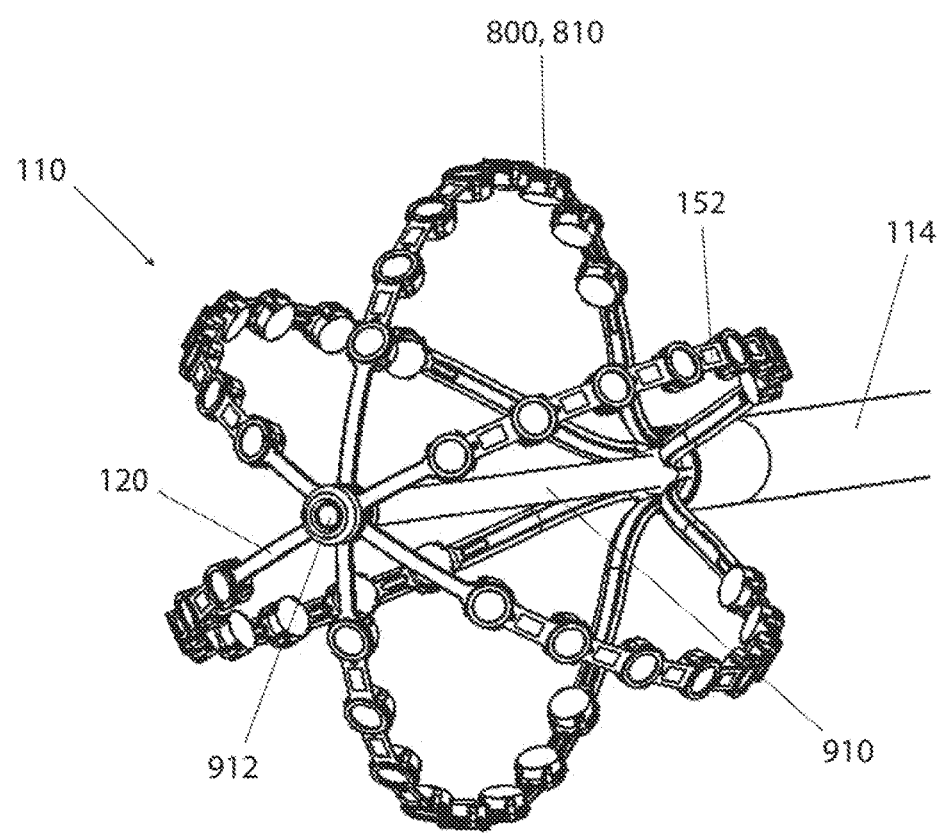
FIG. 9A is a perspective view of an embodiment of a flex-PCB catheter, in accordance with aspects of the inventive concepts.

FIG. 9A is a perspective view of an embodiment of a flex-PCB catheter, in accordance with aspects of the inventive concepts. In the embodiment of FIG. 9A, the expandable assembly 110 includes a plurality of splines 120 configured as shown in the embodiment of FIG. 8. In this embodiment, the ultrasound transducers 800 are coupled to the splines 120 using a housing 810. However, in other embodiments, the ultrasound transducers 800 could be coupled to the splines 120 in different manners and/or different electronic elements could be included.

In this embodiment, an array of ultrasound transducers 800 and sensing electrodes 152 are substantially equally distributed across a number of splines 120—shown in an expanded state. Proximal ends (nearest the shaft 114) of the splines 120 are attached to a distal end of the shaft 114, such as at a location on or within shaft 114, or between shaft 114 and an inner, translatable (i.e. advanceable and retractable) shaft 910. Distal ends of the splines 120 are connected to distal end of inner shaft 910, which is retracted and advanced to expand and collapse, respectively, the expandable assembly 110. Inner shaft 910 can be advanced and retracted via a control on a proximal handle, such as control 113 of handle 112 of FIG. 1. Inner shaft 910 can include a lumen 912, such as a lumen constructed and arranged to receive a guidewire.

Figure 9B:
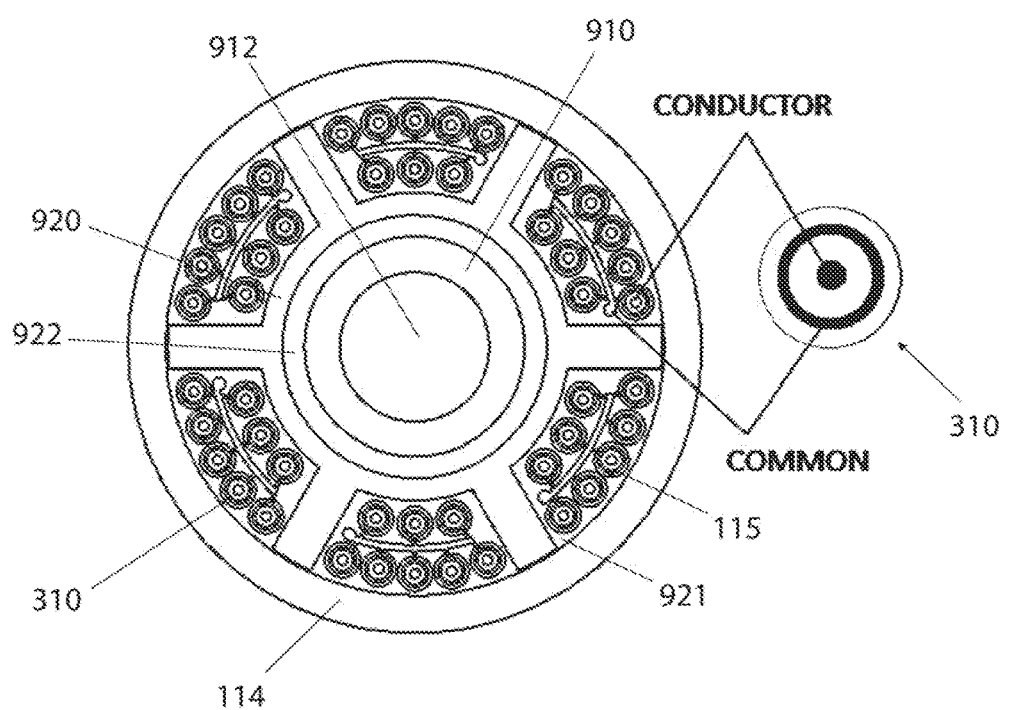
FIG. 9B is a front view of an embodiment of the flex-PCB catheter of FIG. 9A in a collapsed state within an outer shaft, in accordance with aspects of the inventive concepts.

FIG. 9B is a sectional view of a shaft portion of an embodiment of flex-PCB catheter of FIG. 9A, in accordance with aspects of the inventive concepts.

There are three different tubes in this embodiment. The outer tube or $1^{st}$ tube is shaft 114, which surrounds the other two tubes as well as micro coax cables 310. Shaft 114 can comprise a diameter and otherwise be constructed and arranged to be inserted through a transseptal sheath or other introduction device, such as introducer 10 of FIG. 1, to deliver the flex-PCB catheter 100 internal to the body. The $2^{nd}$ tube, shaft 920 comprises a tube with multiple radially outward facing projections which effectively create multiple lumens 921 between shaft 114 and shaft 920 (e.g. the 6 lumens shown in FIG. 9B). In some embodiments, lumens 921 comprises between 2 and 12 lumens. In some embodiments, shaft 114 and shaft 920 comprises a single structure, such as a single extrusion of plastic material made from a die that creates the lumens 921.

Lumens 921 house and segregate/group the wires 115 (e.g., micro coax cables 310). Shaft 114, inner shaft 910 and/or lumens 921 provide radial support to flex-PCB catheter 100. Shaft 920 includes a central lumen, channel 922, for a 3rd tube, an inner, translatable shaft 910. The inner shaft 910 includes lumen 912 which can be configured to receive a guidewire for over-the-wire insertion of flex-PCB catheter 100 into or out of a body, such as into or out of a heart chamber. Alternatively or additionally, lumen 912 can be used to pass a second electrode, to inject fluid, such as contrast media, or the like. The lumen 912 extends from at least a proximal end of the shaft 114 (e.g. from the handle 112, shown in FIG. 1) to a distal end of shaft 114. Shaft 910 can be operably connected to a control on a handle, such as control 113 of handle 112 of FIG. 1.

In various embodiments, advantages of the flex-PCB catheter 100 include: a 360×360 isochronal map of electrical activity of the heart, rapid acquisition of cardiac chamber geometry, low profile insertion/retraction (e.g. due to staggered connection points as described hereinabove), enhanced flexibility (e.g. due to the flexible PCB construction), reduced cost (e.g. due to the flexible PCB construction), and variable profile. "Over-the-wire" design facilitates safe, efficient catheter placement to a body location, such as within a heart chamber. The flex-PCB approach enables cost-reduced, efficient and compact electrical communication among elements of the flex-PCB catheter.

In various embodiments, the $1^{st}$ tube (shaft 114) has an outer diameter less than about 15 Fr, such as less than 11 Fr or less than 9 Fr, such as to be introduced through a 15 Fr, 11 Fr or 9 Fr transseptal sheath. Inner shaft 910 can be configured to be advanced over a 0.032" to 0.038" diameter interventional guidewire.

In various embodiments, 1 to 12 splines can be used, with 6 splines presently preferred. When 6 splines are used, the angle between each pair of splines can be similar, i.e. approximately 60° with 6 splines to achieve 360° coverage. With a different number of splines, a different angle between splines could be used. In some embodiments, dissimilar angular separation between splines can be employed.

In various embodiments, a diameter of expandable assembly 110 in its expanded state is about 1 to 4 cm, but about 2.5 cm is presently preferred.

Various materials can be used for construction of various devices discussed herein. For example, the splines can comprise or be made from nickel titanium alloy, which is presently preferred, stainless steel, cobalt chromium, and some rigid plastics, such as polyimide or PEEK, as examples.

The expandable assembly 110 can include an array of components. For example, the flex-PCB substrate is provided with ceramic PZT material for ultrasound, and gold pads for electrodes, e.g., coated with impedance lowering coatings, such as PEDOT or IrOx.

One or more of the shafts, e.g., outer shaft 114, inner shaft 910, and/or multi-lumen shaft 920, can be comprised of a metal or plastic braid (e.g. a stainless steel braid), with flat wire preferred, encapsulated by a thermoplastic material (e.g., Pebax, Nylon, Polyurethane) with an inner lubricious liner (e.g., PTFE, FEP, Nylon).

Figure 10:
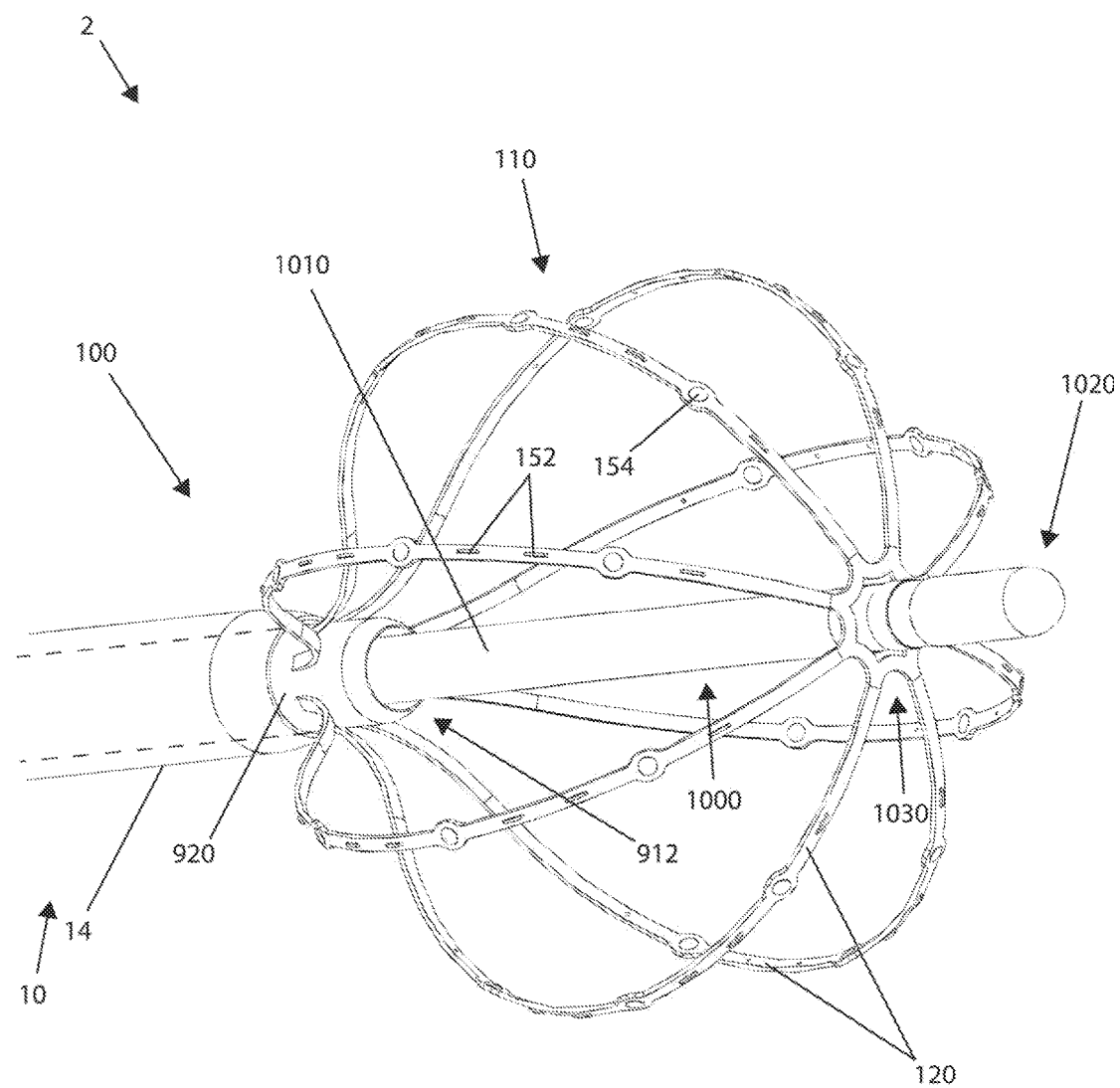
FIG. 10 is a perspective view of another embodiment of a flex-PCB catheter, in accordance with aspects of the inventive concepts.

Referring now to FIG. 10, a perspective view of the distal portion of a system 2 for diagnosing and/or treating a heart arrhythmia or other heart condition, such as atrial fibrillation and/or ventricular tachycardia, is illustrated. The system 2 includes an introducer 10, a flex-PCB catheter 100 and an ablation catheter 1000. Introducer 10 can be configured similar to introducer 10 of FIG. 1, including shaft 14 sized to slidingly receive flex-PCB catheter 100. Flex-PCB catheter 100 comprises a shaft 920, and catheter 1000 includes a shaft 1010. Shaft 920 includes an inner lumen 912 configured to slidingly receive shaft 1010 of catheter 1000. Shaft 920 can be of similar construction to shaft 114 of FIG. 1, with the addition of lumen 912.

The diagnostic flex-PCB catheter 100 and catheter 1000 are constructed and arranged for insertion into a body location, such as the chamber of a heart. Shafts 920 and 1010 are typically constructed of sufficiently flexible material to allow insertion through the tortuosity imposed by the patient's vascular system. Attached to the distal end of shaft 920 is expandable assembly 110, which can be of similar construction to expandable assembly 110 of FIG. 1. As shown in FIG. 10, expandable assembly 110 has been advanced from the distal end of shaft 14 of introducer 10 such that expandable assembly 110 is radially expanded. Expandable assembly 110 includes a plurality of electrodes 152 and a plurality of ultrasound transducers 154 on splines 120 forming a basket array or basket catheter, in this embodiment. In the embodiment of FIG. 10, two electrodes 152 are positioned between some pairs of ultrasound transducers 154. Any number, ratio and placement of electrodes 152, ultrasound transducers 154, and/or other electronic elements (e.g. other sensors or transducers) can be included. Expandable assembly 110 includes a ring-shaped opening on its distal end, opening 1030 sized and positioned to allow the distal end of catheter 1000 to exit there through.

Shaft 1010 of ablation catheter 1000 includes at least one ablation element 1020, positioned at the tip or otherwise on a distal portion of shaft 1010. Ablation element 1020 is constructed and arranged to deliver energy to tissue, such as when ablation catheter 1000 is attached to a source of energy, such as radiofrequency energy and/or other energy type in accordance with known principles.

In various embodiments, the flex-PCB catheter 100, as a diagnostic catheter, can be used for mapping tissue, such as an organ or portion of an organ (e.g. a portion of a heart wall). The flex-PCB catheter 100 can include one or more ultrasound transducers, such as ultrasound transducers 154, these transducers used to provide two or three dimensional distance information such as distance information used to create a two or three dimensional map of tissue, determine relative position of tissue such as tissue walls and/or determine device locations such as relative locations of one or more portions of a device of system 2 or another device. The flex-PCB catheter 100 can include one or more electrodes, such as one or more electrodes 152, such as electrodes used to record physiologic electric activity such as electrical activity of the heart, or to measure a transmitted electrical signal such as a signal used to measure a distance between the electrode and another electrode. Three dimensional anatomical mapping information collected by flex-PCB catheter 100 can be used by the electronic module 360 of FIG. 3B to create a three dimensional display of an anatomical location of which at least a portion is to be treated by ablation catheter 1000. For example, the flex-PCB catheter 100 can be coupled to a computer system configured to display anatomical mapping information generated by the flex-PCB catheter 100, such as volumes, locations, shapes, contours, and movement of organs, nerves, and other tissue within the body. The flex-PCB catheter 100 can be coupled to the computer system to display the electrical mapping information, such as to display dipole mapping or other information, as an example.

Additionally, the location of ablation catheter 1000 or other inserted devices can be displayed, such as their position relative to tissue or the flex-PCB catheter 100. For example, flex-PCB catheter 100 can be used to map the heart, while ablation catheter 1000 can be directed to a tissue location in the heart targeted for treatment (e.g. targeted for treatment based on information provided by the flex-PCB catheter 100). For example, ablation catheter 1000 can be configured to ablate cardiac tissue to treat a patient suffering from a cardiac arrhythmia, such as atrial fibrillation, atrial flutter, supraventricular tachycardias (SVT), Wolff-Parkinson-White syndrome, and ventricular tachycardias (VT). An ablation catheter is described herein as a form of a treatment device for purposes of conveying aspects of the invention, but a different type of treatment device (e.g., a pacing device; a defibrillation device; a stent delivery device; a drug delivery device, a stem cell delivery device, or the like) can be used in other embodiments in combination with flex-PCB catheter 100. In some embodiments, one or more of these treatment devices can be inserted through the lumen 912 of the flex-PCB catheter 100.

In some embodiments, the flex-PCB catheter 100 can be configured to access the left atrium of the patient while utilizing a single transseptal puncture through which all the catheter components can access the left atrium (and subsequently the left ventricle in some cases). In other embodiments, the flex-PCB catheter 100 can be configured to access the left ventricle of the patient while utilizing a single crossing of the aortic valve through which all the catheter components access the left ventricle (and subsequently the left atrium in some cases).

In some methods, shaft 14 is inserted through the atrial septum and into the left atrium, followed by the insertion of the flex-PCB catheter 100 through a lumen of shaft 14. Subsequently, ablation catheter 1000 is inserted through the lumen 912 of shaft 920. In other methods, shaft 14 is inserted into the left atrium, followed by the simultaneous insertion of the flex-PCB catheter 100 and ablation catheter 1000 (e.g. the flex-PCB catheter 100 is inserted with ablation catheter 1000 residing at least partially within lumen 912). In some embodiments, shaft 14 can include or be a steerable sheath. In some embodiments, the flex-PCB catheter 100 and/or ablation catheter 1000 are steerable, so that manual, semi-automatic, or automatic steering can be performed by an operator and/or a robotic control assembly.

The flex-PCB catheter 100 can be positioned in the left atrium and can provide information selected from the group comprising: electrical information, such as surface charge information, anatomical geometry information, such as heart wall surface information or heart wall thickness information, other physiologic and anatomical information, such as those known in the art, and combinations of these. Shaft 920 of the flex-PCB catheter 100 can be configured to be inserted into the heart via the venous system, for example a vein in a leg or a vein in a neck. Shaft 920 can include a braid within its outer and inner surfaces, not shown, but typically a braid of plastic or metal fibers that enhance the structural integrity and performance of shaft 920. In some embodiments, the braid of shaft 920 can include conductors, such as wires 115 of FIG. 1.

In various embodiments, the inserted catheter or other elongated device inserted through lumen 912 can include another catheter, such as a diagnostic catheter configured to record signals from a location selected from a group comprising: the left atrium, the right atrium, the Bundle of HIS, the right ventricular apex, a pulmonary vein, and the coronary sinus. Alternatively or additionally, the inserted catheter can comprise another type of catheter device.

In various embodiments, the expandable assembly 110 is constructed and arranged to be biased in the expanded shape shown in FIGS. 9A and 10, as examples. The expanded geometry of expandable assembly 110, including at least two or more splines 120 in an expanded or partially expanded state, can be described as a "basket" having a substantially hollow center and spaces between adjacent splines 120. In the illustrated embodiment, the basket is spherical, but can include any suitable shape, for example an ellipsoid. Thus, in other embodiments, expandable assembly 110 can comprise different shapes or combination of shapes, such as an array of splines 120 where two or more splines 120 comprise similar or dissimilar shapes, dimensions or configurations. In some embodiments, two or more splines 120 can include a varied radius of curvature.

As discussed above, the expandable assembly 110 can be biased in an expanded or collapsed (non-expanded or contracted state). In an example, expandable assembly 110 can be self-expanding such that splines 120 are resiliently biased in the curved geometry shown in FIGS. 9A and 10. Expandable assembly 110 can automatically expand when it exits the distal end of shaft 14, such as by retraction and/or advancement, respectively, of a shaft, such as shaft 920 of FIG. 9A.

Each spline 120 can include a similar or dissimilar arrangement of electrodes 152 and/or ultrasound transducers 154 as an adjacent spline 120 or any other spline 120 in expandable assembly 110. In some embodiments, expandable assembly 110 includes eight splines 120, where each spline 120 can include two to eight electrodes 152 and two to eight ultrasound transducers 154. In some embodiments, expandable assembly 110 includes six splines 120, where each spline 120 can include eight electrodes 152 and eight ultrasound transducers 154. In some embodiments, one or more splines 120 include a number of electrodes 152 that is greater or less than the number of ultrasound transducers 154 that are included on that spline 120. For example, a spline 120 can include seven electrodes 152 and either six or eight ultrasound transducers 154. In some embodiments, a set of electrodes 152 and ultrasound transducers 154 can be arranged in an alternating arrangement, such that one or more single ultrasound transducers 154 lies between two electrodes 152. In some embodiments, some sets of electrodes 152 and ultrasound transducers 154 can be arranged such that one or more single electrodes 152 is positioned between two ultrasound transducers 154.

In various embodiments, electrodes 152 can be configured to record electric signals, such as voltage and/or current signals. The recorded signals can be used to produce electrogram information, dipole mapping information, distance information, such as the distance between any device and/or component of system 2, and other information or combinations of information described in detail herein. Any or all electrodes 152 can comprise a dipole mapping electrode, such as an electrode with an impedance or other electrical property configured to provide information related to surface charge or other dipole mapping parameter.

In some embodiments, the electrodes 152 are of sufficiently low impedance, e.g., in the range less than 10,000 ohms, such as to achieve high-fidelity recording of signal frequencies greater than or equal to 0.1 Hz. In some embodiments, one or more electrodes 152 include an iridium oxide coating, such as to reduce the impedance of electrodes 152.

Alternatively or additionally, numerous forms of coatings or other treatments can be included with one or more electrodes 152, such as a platinum black coating or a carbon nanotube layer. In addition or as an alternative to recording electric signals, electrodes 152 can be constructed and arranged to deliver electric energy, such as radiofrequency energy. In some embodiments, flex-PCB catheter 100 can deliver therapy, such as an ablation therapy delivered to tissue, in addition to its function as a diagnostic catheter, e.g. providing electrical, anatomical and/or device mapping information. In some embodiments, one or more electrodes 152 each comprise one or more coils, such as when the one or more coils are configured to create one or more magnetic fields.

In various embodiments, electrodes 152 can include various materials, such as non-polarizing metals and/or polarizing metals. In some embodiments, one or more electrodes 152 comprise at least one non-noble metal such that electrodes 152 oxidize when in contact with at least one of blood, blood plasma or saline solutions. In some embodiments, electrodes 152 include a coating, for example a coating selected from a group comprising: a metal oxide coating, a conductive polymer coating, and combinations of these. In some embodiments, one or more electrodes 152 can include an outer layer and an inner layer, such as when the outer layer comprises an impedance lowering coating or other layer and the inner layer comprises a layer configured to bond the outer layer to the metallic and/or other remaining portion of the one or more electrodes 152.

In some embodiments, the ultrasound transducers 154 can be configured to record distance information, such as the distance between any device and/or component of the flex-PCB catheter 100 and tissue, such as cardiac wall or other solid tissue. Ultrasound transducers 154 can include a construction comprising: single or multi-element piezoelectric ceramics, piezoelectric micro-machined ultrasound transducers (pMUT), capacitive micro-machined ultrasound transducers (cMUT); piezoelectric polymers, and combinations of these, as examples.

The ablation element 1020 of the ablation catheter 1000 can include a functional element selected from a group comprising: one or more electrodes, a vessel configured to deliver cryogenic energy, a laser diode, an optical fiber configured to deliver ablative energy, a microwave energy delivery element, an ultrasound energy delivery element, a drug, stem cell, or other agent delivery element, a mechanical or other ablation device delivery element, and combinations of these. In the case where ablation element 1020 includes one or more electrodes, the electrodes can include electrodes constructed and arranged to deliver radiofrequency (RF) energy. In the case of multiple electrodes, the electrodes can be configured for bipolar RF energy delivery. Ablation catheter 1000 can be operably connected to an external device configured to deliver energy to ablation element 1020, such electronic module 360 of FIG. 3B. Typical energy delivered by ablation element 1020 comprises an energy selected from a group comprising: electromagnetic energy, such as radiofrequency energy, cryogenic energy, laser energy, light energy, microwave energy, ultrasound energy, chemical energy, and combinations of these.

Similar to the introducer 10 and shaft 14, flex-PCB catheter 100 and/or ablation catheter 1000 can be steerable, such as via a pull wire and anchor, as is known in the art. Ablation catheter 1000 can be steered and advanced by an operator, such as a clinician, so as to exit at any opening of the expandable assembly 110, including the space between two splines 120 or through opening 1030, such as to be further advanced to contact and ablate cardiac tissue.

While the foregoing has described what are considered to be the best mode and/or other preferred embodiments, it is understood that various modifications can be made therein and that the invention or inventions can be implemented in various forms and embodiments, and that they can be applied in numerous applications, only some of which have been described herein. It is intended by the following claims to claim that which is literally described and all equivalents thereto, including all modifications and variations that fall within the scope of each claim.

What is claimed is:

1. A device configured to be inserted into a body lumen, comprising:
    an elongate shaft comprising a proximal end and a distal end;
    an expandable assembly disposed at the distal end of the shaft and configured to transition from a radially compact state to a radially expanded state;
    a flexible printed circuit board (flex-PCB) substrate forming at least a portion of the expandable assembly;
    a plurality of electronic elements coupled to the flex-PCB substrate and configured to at least one of receive or transmit electrical signals; and
    a plurality of communication paths positioned at least one of on or within the flex-PCB substrate and selectively coupling the plurality of electronic elements to a plurality of electrical contacts configured to electrically connect to an electronic module configured to process the electrical signals, wherein:
    the plurality of electronic elements comprises a plurality of ultrasound transducers,
    the expandable assembly comprises at least two splines, including a first spline and a second spline, with at least two ultrasound transducers of the plurality of ultrasound transducers mounted to each spline, and
    the at least two ultrasound transducers mounted to the first spline are linearly staggered from at least two ultrasound transducers mounted to the second spline, such that a protrusion one of the ultrasound transducers on the first spline extends between protrusions of the at least two ultrasound transducers on the second spline.

2. The device of claim 1, wherein the expandable assembly is further configured for insertion into a heart chamber.

3. The device of claim 1, wherein at least some of the plurality of electronic elements are fixedly attached to the flex-PCB substrate.

4. The device of claim 1, wherein at least some of the plurality of electronic elements are fixedly attached to the expandable assembly.

5. The device of claim 1, wherein at least one of the plurality of electronic elements further comprises at least one element selected from the group consisting of: an electrode; a sensor; a transducer; a heating element; a cooling element; and combinations of two or more thereof.

6. The device of claim 1, wherein the plurality of electronic elements further comprises at least one electrode.

7. The device of claim 6, wherein the plurality of electronic elements comprises at least four electrodes and at least four ultrasound transducers.

8. The device of claim 1, wherein the plurality of electronic elements comprises at least one electrode comprising a conductive coating.

9. The device of claim 8, wherein the conductive coating is selected from the group consisting of: iridium oxide; platinum black; PEDOT; carbon nanotubes; and combinations of two or more thereof.

10. The device of claim 1, wherein:
the flex-PCB substrate comprises an electrically conductive pad and at least one of the plurality of ultrasound transducers is electrically connected to the electrically conductive pad.

11. The device of claim 10, further comprising a housing configured to maintain the at least one ultrasound transducer in electrical contact with the conductive pad.

12. The device of claim 1, wherein:
at least one of the plurality of ultrasound transducers comprises a matching layer, an active element on the matching layer, and a backing material on the active element.

13. The device of claim 12, wherein the matching layer is a quarter-wave matching layer based on immersion in blood.

14. The device of claim 1, wherein the expandable assembly comprises a spline support, and the flex-PCB substrate is attached to the spline support in one or more locations.

15. The device of claim 1, wherein the flex-PCB substrate comprises materials selected from the group consisting of: polyimide; polyester; nylon; polyether block amide; liquid crystal polymer; and combinations of two or more thereof.

16. The device of claim 1, wherein the flex-PCB substrate comprises a first layer with a first set of conductors, a second, opposing layer, with a second set of conductors, and at least one via between the first layer and the second layer.

17. The device of claim 1, wherein the plurality of electronic elements further comprises at least one electronic element selected from the group consisting of: a multiplexer; a transducer; a sensor; an A/D converter; a D/A converter; an electric to optical signal converter; an optical to electrical signal converter; an analog signal filter; a digital signal filter; an amplification circuit; a pre-amplification circuit; and combinations of two or more thereof.

18. The device of claim 1, wherein the flex-PCB substrate comprises:
a distal portion positioned on the expandable assembly;
a proximal portion comprising the plurality of electrical contacts; and
a middle portion therebetween comprising at least portions of the plurality of communication paths,
wherein the middle portion extends through at least a majority of a length of the shaft.

19. The device of claim 8, wherein the flex-PCB substrate has a proximal end positioned proximal to the shaft proximal end.

20. The device of claim 1, further comprising at least one communication conduit, wherein the at least one communication conduit comprises a distal end electrically coupled to the flex-PCB substrate and an elongate portion that extends through at least a majority of a length of the shaft.

21. The device of claim 20, wherein the at least one communication conduit comprises a conduit selected from the group consisting of: a wire; a trace; a coaxial cable; a micro coaxial cable; an optical fiber; and combinations of two or more thereof.

22. The device of claim 1, wherein the flex-PCB substrate comprises a plurality of splines, each spline comprising a connection region comprising a series of electrical connection points,
wherein the connection regions are arranged linearly about a central axis of the expandable assembly, and
wherein at least one of the connection regions is staggered with respect to at least one other connection region.

23. The device of claim 22, wherein the plurality of splines are flexibly attached to each other.

24. The device of claim 1, wherein:
the plurality of electronic elements further comprises at least one electrode, and
at least one of the plurality of communication paths is electrically connected to the at least one electrode and at least one of the plurality of ultrasound transducers.

25. The device of claim 24, wherein:
the at least one communication path comprises at least one coaxial cable comprising a shield and an inner conductor, and
the at least one electrode and the at least one ultrasound transducer are electrically connected to the coaxial cable inner conductor.

26. The device of claim 1, wherein the shaft defines an elongate lumen configured to slidingly receive a second device selected from the group consisting of: a guidewire; an ablation catheter; and combinations of two or more thereof.

27. The device of claim 1, wherein the expandable assembly is attached to the distal end of the shaft.

28. The device of claim 1, wherein the shaft comprises a distal portion and wherein the expandable assembly is mounted to the shaft distal portion.

29. The device of claim 1, wherein the expandable assembly is biased in the radially expanded state.

30. The device of claim 1, wherein the expandable assembly is biased in the radially compact state.

* * * * *